(12) United States Patent
Tavernier et al.

(10) Patent No.: US 11,237,174 B2
(45) Date of Patent: *Feb. 1, 2022

(54) METHOD FOR DETECTING PROTEIN-PROTEIN INTERACTIONS IN A CELL UTILIZING PARTICLE-FORMING POLYPEPTIDE-BAIT FUSION PROTEINS AND VIRUS-LIKE PARTICLES

(71) Applicants: VIB VZW, Ghent (BE); Universiteit Gent, Ghent (BE)

(72) Inventors: Jan Tavernier, Balegem (BE); Sven Eyckerman, Nazareth (BE)

(73) Assignees: VIB VZW, Gent (NL); Universiteit Gent, Gent (NL)

( * ) Notice: Subject to any disclaimer, the term of this patent is extended or adjusted under 35 U.S.C. 154(b) by 80 days.

This patent is subject to a terminal disclaimer.

(21) Appl. No.: 16/600,672

(22) Filed: Oct. 14, 2019

(65) Prior Publication Data

US 2020/0033357 A1 Jan. 30, 2020

Related U.S. Application Data

(63) Continuation of application No. 14/402,667, filed as application No. PCT/EP2013/060787 on May 24, 2013, now Pat. No. 10,444,245.

(30) Foreign Application Priority Data

May 24, 2012 (EP) .................................... 12169209

(51) Int. Cl.
| | | |
|---|---|---|
| G01N 33/68 | (2006.01) | |
| C07K 14/005 | (2006.01) | |
| C12N 7/00 | (2006.01) | |
| C12N 7/02 | (2006.01) | |
| C12N 7/04 | (2006.01) | |

(52) U.S. Cl.
CPC ....... *G01N 33/6845* (2013.01); *C07K 14/005* (2013.01); *C12N 7/00* (2013.01); *C07K 2319/20* (2013.01); *C07K 2319/43* (2013.01); *C07K 2319/735* (2013.01); *C12N 7/02* (2013.01); *C12N 7/045* (2013.01); *C12N 2710/10023* (2013.01); *C12N 2740/16023* (2013.01); *C12N 2740/16222* (2013.01); *C12N 2760/20222* (2013.01); *C12N 2770/24223* (2013.01); *C12N 2810/6081* (2013.01); *G01N 33/6848* (2013.01); *G01N 2333/15* (2013.01); *G01N 2570/00* (2013.01)

(58) Field of Classification Search
CPC .. G01N 33/6845; G01N 33/6848; C12N 7/00; C12N 7/045; C12N 7/02; C12N 2740/16023; C12N 2710/10023; C12N 2770/24223

See application file for complete search history.

(56) References Cited

U.S. PATENT DOCUMENTS

| | | | |
|---|---|---|---|
| 5,637,463 A | 6/1997 | Dalton et al. | |
| 5,776,689 A | 7/1998 | Karin et al. | |
| 10,444,245 B2 * | 10/2019 | Tavernier | C12N 7/00 |
| 2003/0100021 A1 | 5/2003 | Eyckerman et al. | |
| 2006/0094030 A1 | 5/2006 | Hunt | |
| 2010/0173408 A1 | 7/2010 | Eyckerman et al. | |

FOREIGN PATENT DOCUMENTS

| | | |
|---|---|---|
| WO | 9002809 A1 | 3/1990 |
| WO | 9220791 A1 | 11/1992 |
| WO | 9710330 A1 | 3/1997 |
| WO | 9732017 A1 | 9/1997 |
| WO | 0102551 A2 | 1/2001 |
| WO | 0190188 A2 | 11/2001 |
| WO | 2011057134 A1 | 5/2011 |
| WO | 2013174999 A1 | 11/2013 |

OTHER PUBLICATIONS

Ellington, A., and J. M. Cherry, 1997, Characteristics of Amino Acids, in Curr. Protocols Mol. Biol., John Wiley & Sons, Inc. A.iC.1-A.1C.12.*
Roldao, A., et al., 2010, Virus-like particles in vaccine development, Exp. Rev. Vaccines 9(10):1149-1176.*
Kushnir, N., et al., 2012, Virus-like particles as a highly efficient vaccine platform: Diversity of targets and production systems and advances in clinical development, Vaccine 31:58-83.*
Eyckerman, S., et al., Apr. 2016, Trapping mammalian protein complexes in viral particles, Nat. Comm. 7:11416, pp. 1-8.*
PCT International Search Report and Written Opinion, Application No. PCT/EP2013/060787, dated Aug. 16, 2013, 10 pages.

* cited by examiner

*Primary Examiner* — Jeffrey S Parkin
(74) *Attorney, Agent, or Firm* — Patent Law Works, LLP

(57) ABSTRACT

The disclosure relates to a virus-like particle in which a protein complex is entrapped, ensuring the formation of the protein complex under physiological conditions, while protecting the protein complex during purification and identification. The disclosure further relates to the use of such virus-like particle for the isolation and identification of protein complexes.

11 Claims, 6 Drawing Sheets

Specification includes a Sequence Listing.

Figure 7

```
  1  MDWSFFRVVA MLFIFLVVVE VNSEFRIQVR DYNTKNGTIK WHSIRRQKRE WIKFAAACRE GEDNSKRNPI AKIHSDCAAN QQVTYRISGV
     >>...Signal Peptide....>>                     >>........Propeptide........>>                                                 >>.>
     >........Extracellular Region..................

91  GIDQPPYGIF VINQKTGEIN ITSIVDREVT PFFIYCRAL NSMGQDLERP LELRVRVLDI NDNPPVFSMA TFAGQIEENS NANTLVMLN
     ...Peptide G...>>                            >>..Peptide A...>>                                                              ^
     ^.........Extracellular Region.........
     ^

181  ATDADEPNNL NSKIAFKIIR QEPSDSPMFI INRNTGEIRT MNNFLDREQY GQYALAVRGS DRDGGADGMS AECECNIKIL DVNDNIPYME
                    >>..Peptide F...>>          >>....Peptide D....>>                                                              ^
     ^..........Extracellular Region........
     ^

271  QSSYTIEIQE NTLNSNLLEI RVIDLDEEFS ANWMAVIFFI SGNEGNWFEI EMNERTNVGI LKVVKPLDYE AMQSLQLSIG VRNKAEFHHS
                                                                               >>........Peptide J..........>>
     ^..........Extracellular Region.........
     ^

361  IMSQYKLKAS AISVTVLNVI EGPVFRPGSK TYVVTGNMGS NDKVGDFVAT DLDTGRPSTT VRYVMGNNPA DLLAVDSRTG KLTLKNKVTK
           >>....Peptide B....>>                           >>........Peptide M.........>>....Peptide K.....>>...Peptide L...Peptide I>>
     ^..........Extracellular Region..........
     ^

451  EQYNMLGGKY QGTILSIDDN LQRTCTGTIN INIQSFGNDD RTNTEPNTKI TTNTGRQEST SSTNYDTSTT STDSSQVYSS EPGNGAKDLL
     ^..........Extracellular Region..........                                                                                    ^

541  SDNVHFGPAG IGLLIMGFLV LGLVPFLMIC CDCGGAPRSA AGFEPVPECS DGAIHSWAVE GPQPEPRDIT TVIPQIPPDN ANIIECIDNS
     ^......>> Extracellular Region
                       >> Transmembrane Region
                                        >>..........................Cytoplasmic Region................................          ^

631  GVYTNEYGGR EMQDLGGGER MTGFELTEGV KTSGMPEICQ EYSGTLRRNS MRECREGGLN MNFMESYFCQ KAYAYADEDE GRPSNDCLLI
     ^................................Cytoplasmic Region................................                                         ^

721  YDIEGVGSPA GSVGCCSFIG EDLDDSFLDT LGPKFKKLAD ISLGKESYPD LDPSWPPQST EPVCLPQETE PVVSGHPPIS PHFGTTTVIS
     ^................................Cytoplasmic Region................................                                         ^

811  ESTYPSGPGV LHPKPILDPL GYGNVTVTES YTTSDTLKPS VHVHDNRPAS NVVVTERVVG PISGADIHGM LEMPDLRDGS NVIVTERVIA
     ^................................Cytoplasmic Region................................                                         ^

901  PSSSLPTSLT IHHPRESSNV VVTERVIQPT SGMIGSLSMH PELANAHNVI VTERVVSGAG VTGLSGTTGI SGGIGSSGLV GTSMGAGSGA
                       >>...........>>   Peptide E
     ^................................Cytoplasmic Region................................                                         ^

991  LSGAGISGGG IGLSSLGGTA SIGHMRSSSD HHFNQTIGSA SPSTARSRIT KYSTVQYSK
     ^......................Cytoplasmic Region....................>>
```

METHOD FOR DETECTING PROTEIN-PROTEIN INTERACTIONS IN A CELL UTILIZING PARTICLE-FORMING POLYPEPTIDE-BAIT FUSION PROTEINS AND VIRUS-LIKE PARTICLES

CROSS-REFERENCE TO RELATED APPLICATIONS

This application is a continuation of U.S. patent application Ser. No. 14/402,667, filed Nov. 20, 2014, pending, which is a national phase entry under 35 U.S.C. § 371 of International Patent Application PCT/EP2013/060787, filed May 24, 2013, designating the United States of America and published in English as International Patent Publication WO 2013/174999 A1 on Nov. 28, 2013, which claims the benefit under Article 8 of the Patent Cooperation Treaty to European Patent Application Serial No. 12169209.9, filed May 24, 2012, the entireties of which are hereby incorporated by reference.

TECHNICAL FIELD

The disclosure relates generally to biotechnology, and more particularly to a virus-like particle in which a protein complex is entrapped, ensuring the formation of the protein complex under physiological conditions, while protecting the protein complex during purification and identification. The disclosure further relates to the use of such virus-like particle for the isolation and identification of protein complexes.

BACKGROUND

Protein-protein interactions are an essential key in all biological processes, from the replication and expression of genes, to the morphogenesis of organisms. Protein-protein interactions govern, amongst others, ligand-receptor interaction and the subsequent signaling pathway; they are important in assembly of enzyme subunits, in the formation of biological supramolecular structures such as ribosomes, filaments and virus particles, and in antigen-antibody interactions.

Researchers have developed several approaches in attempts to identify protein-protein interactions. A major breakthrough was obtained by the introduction of the genetic approaches, of which the yeast two-hybrid (Fields and Song, 1989) is the most important one. Although this technique became widely used, it has several drawbacks. The fusion proteins need to be translocated to the nucleus, which is not always evident. Proteins with intrinsic transcription activation properties may cause false positives. Moreover, interactions that are dependent upon secondary modifications of the protein such as phosphorylation cannot be easily detected.

Several alternative systems have been developed to solve one or more of these problems.

Approaches based on phage display do avoid nuclear translocation. WO9002809 describes how a binding protein can be displayed on the surface of a genetic package, such as a filamentous phage, wherein the gene encoding the binding protein is packaged inside the phage. Phages that bear the binding protein that recognizes the target molecule are isolated and amplified. Several improvements of the phage display approach have been proposed, as described, e.g., in WO9220791, WO9710330, and WO9732017.

However, all these methods suffer from the difficulties that are inherent at the phage display methodology: the proteins need to be exposed at the phage surface and are so exposed to an environment that is not physiologically relevant for the in vivo interaction. Moreover, when screening a phage library, there will be a competition between the phages that results in a selection of the high-affinity binders.

U.S. Pat. No. 5,637,463 describes an improvement of the yeast two-hybrid system, whereby it can be screened for modification-dependent protein-protein interactions. However, this method relies on the co-expression of the modifying enzyme, which will exert its activity in the cytoplasm and may modify enzymes other than the one involved in the protein-protein interaction, which may, on its turn, affect the viability of the host organism.

An interesting evolution is described in U.S. Pat. No. 5,776,689, by the so-called protein recruitment system. Protein-protein interactions are detected by recruitment of a guanine nucleotide exchange factor (Sos) to the plasma membrane, where Sos activates a Ras reporter molecule. This results in the survival of the cell that otherwise would not survive in the culture conditions used. Although this method has certainly the advantage that the protein-protein interaction takes place under physiological conditions in the submembrane space, it has several drawbacks. Modification-dependent interactions cannot be detected. Moreover, the method is using the pleiotropic Ras pathway, which may cause technical complications, such as the occurrence of false positives.

A major improvement in the detection of protein-protein interactions was disclosed in WO0190188, describing the so-called Mappit system. The method, based on a cytokine receptor, not only allows a reliable detection of protein-protein interactions in mammalian cells, but also modification-dependent protein interactions can be detected, as well as complex three-hybrid protein-protein interactions mediated by a small compound (Caligiuri et al., 2006). However, although very useful, the system is limited in sensitivity and some weak interactions cannot be detected. Moreover, as this is a membrane-based system, nuclear interactions are normally not detected. Recently, a cytoplasmic interaction trap has been described, solving several of those shortcomings. However, all of these "genetic" systems rely on the overexpression of both interaction partners, which may result in false positives due to the artificial increase in concentration of one or both of the interaction partners.

As an alternative for the genetic protein-protein interaction detection methods described above, biochemical or co-purification strategies, combined with mass spectrometry-based proteomics (Paul et al., 2011; Gingras et al., 2007), can be used. For the co-purification strategies, a cell homogenate is typically prepared by a detergent-based lysis protocol, followed by capture using a (dual) tag approach (Gavin et al., 2002) or via specific antibodies (Malovannaya et al.). The protein complex extracted from the "soup" of cell constituents is then expected to survive several washing steps, mostly to compensate for the sensitivity of contemporary MS instruments, before the actual analysis occurs. There are no clear guidelines on the extent of washing or on available buffers and their stringency. Most lysis and washing protocols are purely empirical in nature and were optimized using model interactions. It is, therefore, hard to speculate on the loss of factors during these steps (false negatives), or the possibility of false interactions due to loss of cellular integrity (false positives). Use of metabolic labeling strategies allows separation between the proteins sticking to the purification matrix, and between the proteins that associate specifically to the bait protein. Depending on the purification conditions and the sensitivity of the MS instruments used, it is no exception to find more than 1000 proteins in the eluted fraction of a gel-free AP-MS experiment.

There is a further need for co-purification techniques, isolating the protein complexes in their physiological environment, but wherein the complex is protected during the further purification and analysis.

The evolutionary stress on viruses promotes highly condensed coding of information and maximal functionality for small genomes. Accordingly, for HIV-1, it is sufficient to express a single viral protein, the p55 GAG protein, to allow the efficient production of virus-like particles (VLPs) from cells (Gheysen et al., 1989; Shioda and Shibuta, 1990). The p55 GAG protein consists of different parts, which are processed by HIV protease upon maturation of the particle into a functional infectious particle. The N-terminal matrix protein part ensures binding to the membrane via myristoylation and ensures budding (Bryant and Ratner, 1990). The Capsid protein forms the cone-shaped viral core after processing, while the nucleocapsid protein and the p6 protein bind to and protect the viral RNA. The p55 GAG protein is highly mobile before accumulation in cholesterol-rich regions of the membrane, where multimerization actually initiates the budding process (Gomez and Hope, 2006). A total of 4000-5000 GAG molecules are required to form a single particle with a size of about 145 nm (Briggs et al., 2004).

BRIEF SUMMARY

Surprisingly, it was found that the p55 GAG protein can be used to trap a bait protein together with its physiological binding partners into VLPs that are budded from human cells. The very mild "extraction" or "abduction" of the protein complex ensures the identification of relevant interacting proteins. After introduction of a simple one-step particle enrichment protocol to speed up the workflow, it was found that this viral particle-based protein-protein interaction trap approach (called "Virotrap") can be used for the detection of binary interactions. The identification of new partners by the coupling of the Virotrap process to MS-based analysis is also shown.

A first aspect of the disclosure is an artificial virus-like particle (called "Virotrap particle"), comprising (1) a viral particle-forming polypeptide, (2) a first interaction polypeptide and (3) a second interaction polypeptide, interacting with the first interacting polypeptide. As explained below, in one preferred embodiment, the viral-forming polypeptide and the first interacting polypeptide may be two different polypeptide domains of a fusion protein (i.e., a fusion protein consisting of at least two polypeptides derived from two different proteins).

In another preferred embodiment, the viral particle-forming polypeptide and the first interacting polypeptide are independent proteins. Besides the first and the second interaction polypeptide, the virus-like particle may comprise other proteins, recruited to first and/or second interaction polypeptides, wherein all the proteins together form one protein complex. "Polypeptide" refers to a polymer of amino acids and does not refer to a specific length of the molecule. This term also includes post-translational modifications of the polypeptide, such as glycosylation, phosphorylation and acetylation. A "virus-like particle," as used herein, is a particle consisting at least of a viral particle-forming protein, but preferably without the viral DNA or RNA. "Viral particle-forming proteins," as used herein, are known to the person skilled in the art and are proteins that allow the assembly of viral particles and, preferably, budding of the particles of the cell. Examples of such particles have been described in the art and include, but are not limited to, particles derived from virus families including Parvoviridae (such as adeno-associated virus), Retroviridae (such as HIV), and Flaviviridae (such as Hepatitis C virus).

In a preferred embodiment, the particle-forming polypeptide may be a modification of the naturally occurring particle-forming protein, such as a deletion and or mutation, as long as they do not inhibit the particle formation. Preferably, the deletion and/or mutation is reducing the binding of the particle-forming polypeptide with host proteins. Preferably, the modification is a fusion protein. Preferably, the viral particle-forming polypeptide, or its modification, forms a viral structure, consisting of a hollow particle, in which the first and second interaction polypeptides are trapped. In a preferred embodiment, the first interaction polypeptide is anchored to the viral structure, ensuring the capturing of the protein complex formed by the first and the second interaction polypeptide into the inside of the virus-like particle. The anchoring may be direct, wherein the fusion partner of the viral particle-forming polypeptide acts as the first interaction polypeptide, or indirect, wherein an independent linker molecule binds to the viral particle-forming polypeptide at one hand, and to a construct comprising the first interaction polypeptide at the other hand ("dimerizing linker") as illustrated in FIG. 1. As a non-limiting example, such a linker may be a molecule as illustrated in FIG. 1, or it may be a bispecific protein or peptide affinity ligand such as an antibody, or in a preferred setting, a bispecific NANOBODY® or ALPHABODY® binding to the viral particle-forming polypeptide at one hand, and to the first interaction polypeptide at the other hand. In case of a direct anchoring, the viral-forming polypeptide and the first interacting polypeptide are two different polypeptide domains of the same protein. Preferably, the viral particle-forming polypeptide is a HIV protein; even more preferably, the viral particle-forming polypeptide is the p55 GAG protein, or a modification or functional fragment thereof. A "modification" or "functional fragment," as used herein, is a modification or functional fragment that is still capable of forming virus-like particles that are capable of entrapping the protein complex according to the disclosure. Preferably, the modification is a fusion protein; even more preferably, the p55 GAG protein is fused to the first interaction polypeptide.

Another aspect of the disclosure is the use of an artificial virus-like particle, according to the disclosure, for the detection of protein-protein interactions.

Still another aspect of the disclosure is a method for detecting protein-protein interactions, the method comprising (1) the expression of a viral particle-forming polypeptide in a cell, (2) recruiting a first interaction polypeptide to the viral particle-forming polypeptide, (3) recruiting a second interacting polypeptide to the first interaction polypeptide, (4) isolation of the virus-like particles, and (5) analysis of the entrapped protein complex. Preferably, the cell is a mammalian cell. Preferably, the analysis of the entrapped protein complex is an MS-based analysis. It is clear for the person skilled in the art that protein-protein interactions of any nature can be detected with the method. As a non-limiting example, the method may be used to detect proteins involved in a signaling network, but it may also be used to detect antigen-antibody interactions, or other affinity-binding proteins and their target(s).

BRIEF DESCRIPTION OF THE FIGURES

FIG. 7: Amino acid sequence of Desmoglein 1 (SEQ ID NO: 26) with annotation of extracellular, transmembrane and cytoplasmic regions, and with mapping of the peptides identified in the Virotrap analysis with S100A1 bait protein.

DETAILED DESCRIPTION

Examples

Materials and Methods

Plasmids and Antibodies

Figure 1:
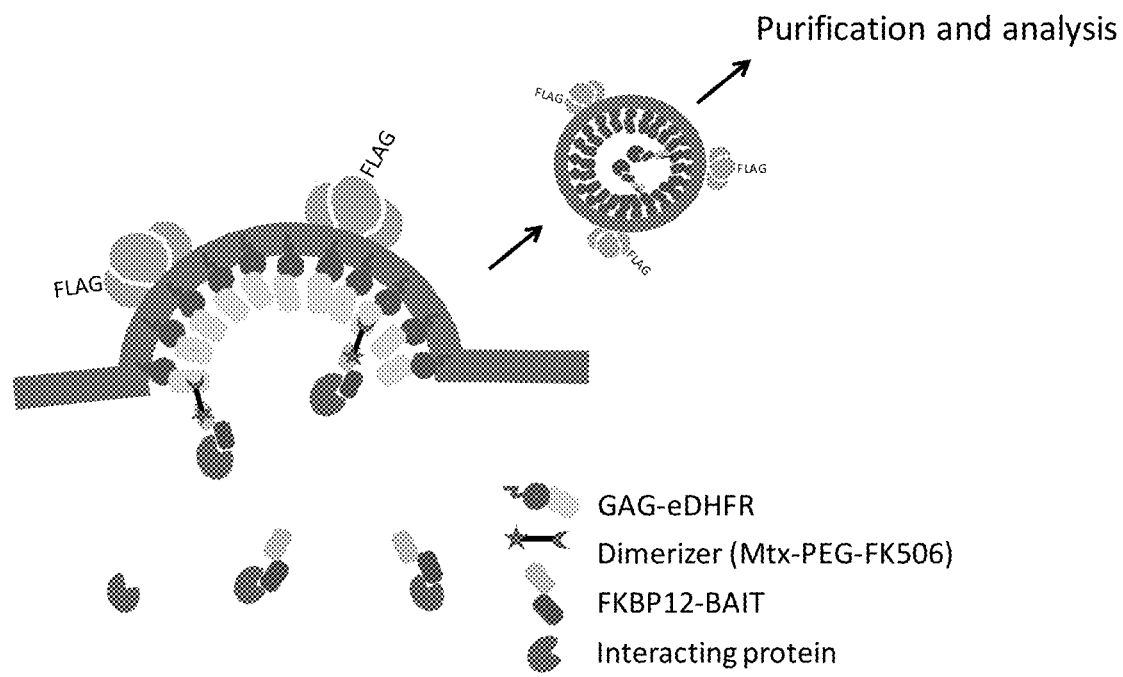
FIG. 1: Principle of conditional protein complex trapping in virotrap particles. A bait protein is fused in frame to FKBP12. Upon addition of Mtx-PEG-FK506 dimerizer, the FKBP12-bait fusion protein is recruited to the GAG-eDHFR fusion protein, leading to trapping of the bait and its interacting proteins in the virotrap particles that are formed by GAG multimerization and budding. Further purification of virotrap particles followed by proteomic analysis results in identification of the interacting proteins.

The p55 GAG fusion constructs were generated by PCR amplification using primers Oligo1 and Oligo2 (see Table 1) of the p55 GAG coding sequence from the pCMV-dR8.74 packaging construct (Addgene) and by subsequent IN-FUSION® reaction (Clontech) in pMG1-Ras, a Ras expression vector used in the MAPPIT system (Eyckerman et al., 2001), resulting in a p55 GAG-RAS under control of the strong SRalpha promoter (pMET7-GAG-Ras). EGFP was transferred from pEGFP-C1 vector (Clontech) to generate the pMET7-GAG-EGFP construct. Using PCR-based cloning, a GATEWAY® cassette was inserted to allow recombination-assisted cloning. The complete set of positive and random reference clones were transferred in a single direction (no bait-prey swap) using standard GATEWAY® cloning. Prey ORFs from these sets were transferred into a GATEWAY®-compatible pMET7 expression vector with an N-terminal E-tag fused in frame.

The pMD2.g pseudotyping vector was kindly provided by D. Trono. The pcDNA3-FLAG-VSV-G and pcDNA3-Etag-VSV-G are described elsewhere (Eyckerman et al., submitted).

Antibodies used for Western blot were anti-p24 GAG (Abcam), anti-FLAG (M2, Sigma Aldrich), anti-actin (Sigma Aldrich) and anti-E-tag (Phadia). Secondary antibodies were from LI-COR, and blots were digitally imaged using an ODYSSEY® Imager system (LI-COR).

Cell Culture, Production and Purification of Virotrap Particles.

HEK293T cells were cultured in a humidified atmosphere at 8% $CO_2$ using high-glucose DMEM (Invitrogen) complemented with 10% FCS and antibiotics.

Cells were transfected overnight the day after seeding with a standard calcium phosphate transfection procedure. For ultracentrifugation experiments, 25 µg of bait vector (GAG-EGFP and GAG-Ras) was transfected and normalized to 50 µg with a mock vector, in $6 \times 10^6$ cells seeded the day before in 75 $cm^2$ bottles. For concentration of the virotrap particles, supernatant was harvested after 24 hours, centrifuged samples for 3 minutes at 1250×g to remove cellular debris and filtered the supernatant through 0.45 mm filters. The samples were then centrifuged in a Beckman ultracentrifuge using a Ti41 swinging bucket rotor at 22000 rpm. The supernatant was discarded and particle pellets were re-suspended directly in loading buffer for Western analysis.

For binary interaction assays, 650,000 HEK293T cells were seeded the day before transfection in six-well plates. On the day of transfection, a DNA mixture was prepared containing the following: 3.5 µg bait construct (pMET7-GAG-bait), 0.8 µg prey construct (pMET7-E-tag prey or pMET7-FLAG-Raf), 0.7 µg pMD2.G and 1.4 µg pcDNA3-FLAG-VSV-G. Following overnight transfection, cells were washed once with PBS and 1 ml of fresh growth medium was added to the wells. Cellular debris was removed from the harvested supernatant by 3 minutes centrifugation at 2000×g. The cleared medium was then incubated with 10 µl DYNABEADS® MyOne™ Streptavidin T1 beads (Invitrogen)pre-loaded with 1 µg monoclonal ANTI-FLAG® BioM2-Biotin, Clone M2 (Sigma-Aldrich®) according to the manufacturer's protocol. After 2 hours binding at 4° C. by end-over-end rotation, beads were washed two times with washing buffer (20 mM HEPES pH 7.4, 150 mM NaCl), and the captured particles were released directly in 35 µl 2×SDS-PAGE loading buffer. A 5-minute incubation step at 65° C. before removal of the beads ensured complete release. After boiling, the samples were loaded on a 10% SDS-PAGE gel, or on commercial 4-12% gradient gels (Biorad), and after separation, the proteins were transferred to HYBOND®-C Extra nitrocellulose membranes (GE Healthcare). Lysates of the producer cells were prepared by direct addition of 200 µl RIPA buffer (50 mM TRIS.HCl pH 7.4, 150 mM NaCl, 1% NP40, 1% sodium deoxycholate, 0.1% SDS+Complete protease inhibitor cocktail [Roche]) to the six-well plates after washing of the cells in chilled PBS. The lysates were cleared by centrifugation at 13000×g, 4° C. for 15 minutes to remove the insoluble fraction.

The PRS and RRS were randomized and processed in sets of about 45 single PPI measurements. Each set was loaded on two 4-12% gradient gels with 26 slots (Biorad). Each set of measurements also contained the GAG-EGFP expression control, a mock control and the interaction between GRAP2 and LCP2 as a positive control for Virotrap functionality. A single pooled positive control for the GRAP2-LCP2 interaction was also loaded on each gel to allow cross-comparison between the gels. Bands were quantified by fluorescence signals with an ODYSSEY® system (LICOR). The detection threshold was based on RRS signals and was determined for each individual gel.

For mass spectrometry, $4.75 \times 10^6$ HEK293T cells seeded in 75 $cm^2$ bottles were transfected the next day with a total of 50 µg DNA. The following DNA quantities were used: GAG-bait 25 µg; mock vector 17.8 µg; 7.2 µg of a 50/50 pMD2.G-pcDNA3-FLAG-VSV-G mix. The cellular supernatant was harvested after 32 hours and was centrifuged for 3 minutes at 450×g to remove cellular debris. The cleared supernatant was then filtered using 0.45 µm filters (MILLIPORE®). A total of 100 µl MyOne™ Streptavidin T1 beads pre-loaded with 10 µl ANTI-FLAG® BioM2-Biotin antibody was used to bind the tagged particles. Particles were allowed to bind for 2 hours by end-over-end rotation. Bead-particle complexes were washed once with washing buffer and were then frozen overnight in lysis buffer (PBS, 0.4% CHAPS, 1.2 M guanidine hydrochloride) to release and denature the trapped proteins. After lysis of the particles and removal of the beads, proteins were reduced (10 mM TCEP.HCl, 10 minutes at 37° C.) and alkylated (20 mM Iodoacetamide, 10 minutes at 37° C.). Via NAPS gel filtration columns (GE Healthcare), the protein sample was transferred to 10 mM ammonium bicarbonate buffer. Trypsin digest was performed overnight at 37° C. using 0.5 µg sequence-grade trypsin (Promega). Samples were vacuum dried and resuspended in 2% acetonitrile, separated by nano-LC and directly analyzed with a LTQ® ORBITRAP® Velos instrument (Thermo Scientific). Searches were performed using the MASCOT® algorithm at 99% confidence against the human Swissprot database complemented with HIV-1 and EGFP protein sequences.

Example 1: Generation of the Conditional Trapping Construct

The p55 GAG fusion constructs were generated by PCR amplification using primers Oligo1 and Oligo2 (see Table 1) of the p55 GAG coding sequence from the pCMV-dR8.74 packaging construct (Addgene) and by subsequent IN-FUSION® reaction (Clontech) in a pMET7-gp130-RAS construct (Eyckerman et al., 2001). This resulted in a p55 GAG-fusion construct under control of the strong SRalpha promoter. The plasmid was designated pMET7-GAG-RAS. EGFP was transferred from pEGFP-C1 vector (Clontech) to generate the pMET7-GAG-EGFP construct. The eDHFR fragment was amplified from plasmid pSEL1-eDHFR (Caligiuri et al., 2006) with primers Oligo3 and Oligo4, digested with XhoI and XbaI and cloned in the SalI-XbaI opened pMET7-GAG-RAS backbone, which resulted in pMET7-GAG-eDHFR. The FKBP12 protein was amplified with primers Oligo5 and Oligo6 from pMG2-FKBP12 (Eyckerman et al., 2005). The PCR product was digested with NdeI and XbaI and cloned in the NdeI-XbaI opened pMET7-GAG-eDHFR vector, which resulted in the pMET7-GAG-eDHFR-FKBP12-MCS construct. The reverse primer Oligo6 also encoded a flexible Gly-Gly-Ser hinge sequence and contained a number of restriction enzyme recognition sites. This multi-cloning site (MCS) allows different cloning strategies for the C-terminal fusion of a bait protein. The primers Oligo7 and Oligo8 were annealed and ligated into the NdeI-MluI opened pMET7-GAG-eDHFR-FKBP12-MCS construct to insert a FLAG tag sequence and a T2A auto-processing site. This resulted in pMET7-GAGeDHFR-T2A-FLAG-FKBP12-MCS. The Thosae asigna 2A (T2A) auto-processing sequence ensures, by a ribosomal skip mechanism (Szymczak et al., 2004), the complete cleavage of the fusion protein resulting in two protein fragments upon translation: the GAG-eDHFR part and the FKBP12-MCS part. The EcoRI site that was present within the eDHFR coding sequence was removed by using site-directed mutagenesis (QUICKCHANGE™ Site-Directed Mutagenesis kit, Stratagene) with Oligo9 and Oligo10 on pMET7-GAG-eDHFR-T2A-FLAG-FKBP12-MCS, resulting in the pMET7-VT1-MCS construct.

The GATEWAY® cassette (Invitrogen) was amplified by primers Oligo11 and Oligo12 from pMG1-Gateway (Braun et al., 2009), and cloned via MfeI-XbaI in the EcoRI-XbaI opened pMET7-VT1-MCS plasmid, which resulted in the pMET7-VT1-GW destination vector. The coding sequence for CSK1B was transferred via the GATEWAY® LR reaction from the Positive Reference Set described in Braun et al. (Braun et al., 2009) into the pMET7-VT1-GW destination vector resulting in pMET7-VT1-CSK1B. The coding sequence for CDK2 was transferred by the LR reaction to a pMET7-Etag-GATEWAY® construct (Lievens et al., unpublished) leading to pMET7-Etag-CDK2.

The pcDNA3-FLAG-VSV-G construct used for purification was generated as described (Eyckerman et al., submitted). The pMD2.G construct expressing VSV-G under control of a strong CMV promoter was provided by Didier Trono (EPFL, Lausanne, Switzerland).

The chemical bivalent molecule or dimerizer consists out of methotrexate (Mtx) and FK506 linked via a PolyEthylene Glycol (PEG) linker, and was prepared as described in Caligiuri et al., 2006.

TABLE 1

Oligonucleotides used for the generation of the pMET7-VT1 constructs.

| Number | Sequence | Use | SEQ ID NO |
|---|---|---|---|
| Oligo1 | CTCTAAAAGCTGCGGGGCCCGCTAGCGCCACCATGGGTGCGAGAGCGTCAG | GAG amplification | 1 |
| Oligo2 | TGTATTCGGTGAATTCTGAGCTCGTCGACCCGCCTTGTGACGAGGGGTCGCTGC | GAG amplification | 2 |
| Oligo3 | GCGACTCGAGCGGAATCAGTCTGATTGCGG | eDHFR amplification | 3 |
| Oligo4 | CGCTTCTAGATTACATATGGCCGCTGCCCCGCCGCTCCAGAATCTC | eDHFR amplification | 4 |
| Oligo5 | GCGACATATGGGCACGCGTGTGCAGGTGGAAACCATCTC | FKBP 12 amplification | 5 |
| Oligo6 | CGCTTCTAGATTACTCGAGTGCGGCCGCGAATTCTGAGCTCGTCGACCCGCCTTCCAGTTTTAGAAGCTCC | FKBP 12 amplification | 6 |
| Oligo7 | TATGGAGGGCAGAGGCAGCCTGCTGACCTGCGGCGACGTGGAGGAAAACCCCGGCCCCGATTACAAGGATGACGACGATAAGA | T2A and FLAG sequence annealing | 7 |
| Oligo8 | CGCGTCTTATCGTCGTCATCCTTGTAATCGGGGCCGGGGTTTTCCTCCACGTCGCCGCAGGTCAGCAGGCTGCCTCTGCCCTCCA | T2A and FLAG sequence annealing | 8 |
| Oligo9 | GAATCGGTATTCAGCGAGTTCCACGATGCTGATG | EcoRI mutagenesis | 9 |
| Oligo10 | CATCAGCATCGTGGAACTCGCTGAATACCGATTC | EcoRI mutagenesis | 10 |
| Oligo11 cassette amplification | CCCCAATTGACAAGTTTGTACAAAAAAGC | GATEWAY® | 11 |
| Oligo12 cassette amplification | GGGTCTAGATCAAACCACTTTGTACAAG | GATEWAY® | 12 |

Example 2: Production, Harvest and Western Blot Analysis

For production of virotrap particles, a co-transfection in HEK293T cells was performed via the Ca-Phosphate precipitation method. HEK293T cells were cultured in DMEM medium (Gibco) and 10% FCS at 37° C. in a humidified atmosphere with 5% $CO_2$. The day before transfection, 650,000 cells were seeded in a six-well plate. On the day of transfection, a DNA mixture was prepared containing the following:
0.7 µg pMD2.G
1.4 µg pcDNA3-FLAG-VSV-G
0.8 µg pMET7-Etag-CDK2
3.5 µg pMET7-VT1-CKS1B or pMET7-VT1-EGFP
15 µl of 2.5 M $CaCl_2$ Water was added to a total volume of 150 µl.

The DNA mixture was then added dropwise to 150 µl 2× HeBs solution while vortexing. The transfection mix was brought on the cells and the precipitates were left overnight for transfection. Following transfection, the cells were washed once with PBS and 1 ml of fresh growth medium was added with either 5 or 10 µM of dimerizer, or without dimerizer. The production medium was harvested after 24 hours. Cellular debris was removed by one minute centrifugation at 2000×g. The cleared medium was then incubated with 10 µl DYNABEADS® MyOne™ Streptavidin T1 beads (Invitrogen) loaded with 1 µg monoclonal ANTI-FLAG® BioM2-Biotin, Clone M2 (Sigma-Aldrich®) according to the manufacturer's protocol. After 2 hours binding at 4° C. by end-over-end rotation, beads were washed two times with washing buffer (20 mM HEPES pH 7.4, 150 mM NaCl), and the captured nanoparticles were released directly in 35 µl 2×SDS-PAGE loading buffer. The samples were incubated for 5 minutes at 65° C. to ensure complete denaturation/release of the virotrap particles. After removal of the beads and boiling, the samples were loaded on a 10% SDS-PAGE gel, and after separation, the proteins were transferred to HYBOND®-C Extra nitrocellulose membranes (GE Healthcare). Lysates of the producer cells were prepared by direct addition of 200 µl RIPA buffer (50 mM TRIS.HCl pH 7.4, 150 mM NaCl, 1% NP40, 1% sodium deoxycholate, 0.1% SDS+Complete protease inhibitor cocktail [Roche]) to the six-well plates after washing of the cells in chilled PBS. The lysates were cleared by centrifugation at 13000×g, 4° C. for 15 minutes to remove the insoluble fraction. Western blots were probed with mouse anti-E tag (Phadia, 1/1000), mouse anti-GAG (Abcam, 1/1000) or rabbit anti-VSV-G (Sigma/Aldrich, 1/5000). Secondary antibodies were from LI-COR, and blots were digitally imaged using an ODYSSEY® Imager system (LI-COR).

Example 3: The pMET7-VT1 Construct

Figure 2:
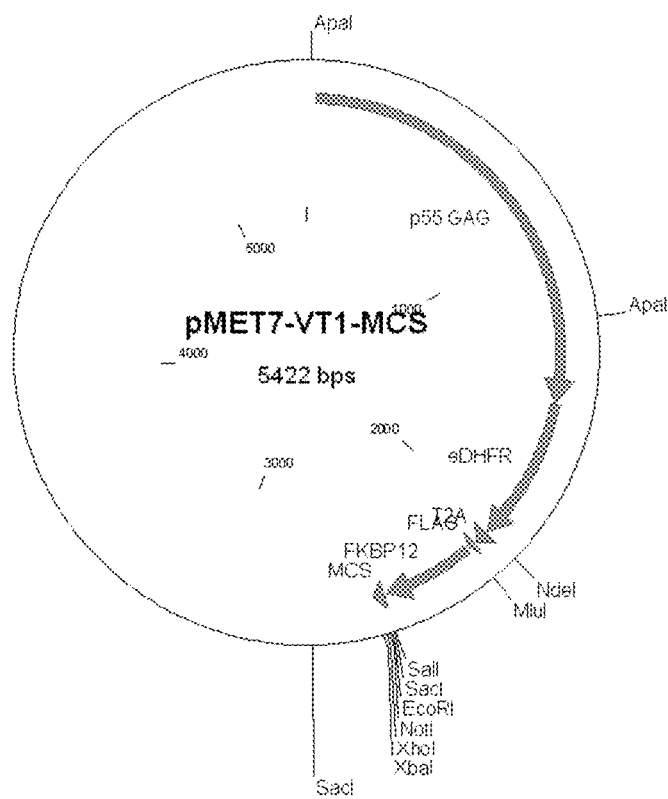
FIG. 2: Plasmid map for the pMET7-VT1-MCS vector. Transfer of the coding sequences for EGFP led to the pMET7-VT1-EGFP vector, respectively, transfer of the GATEWAY® cassette resulted in the pMET7-VT1-GW, which then allowed transfer of the CSK1B coding sequence from a GATEWAY® entry clone, leading to pMET7-VT1-CKS1B. MCS: multi-cloning site

First, a plasmid for expression of the bait construct was generated. The p55 GAG fragment was cloned in the pMET7 vector, which drives expression via the strong SRα promoter. The *E. coli*-derived Dihydrofolate reductase (DHFR) protein was fused C-terminally of GAG while the FK506-Binding Protein 12 (FKBP12) coding sequence was cloned via a T2A auto-processing site and a FLAG-tag, in frame and C-terminal of DHFR. The GAG-eDHFR-T2A-FKBP12 expression construct was followed by a multi-cloning site to allow efficient transfer of bait proteins into this expression vector (FIG. 2).

A GATEWAY® cassette and an EGFP expression construct were inserted in the MCS of pMET7-VT1-MCS by standard cloning procedures. The CSK1B protein was transferred via the GATEWAY® LR reaction into the pMET7-VT1-GATEWAY® construct.

Example 4: Test of the CKS1B-CDK2 Interaction

Figure 3:
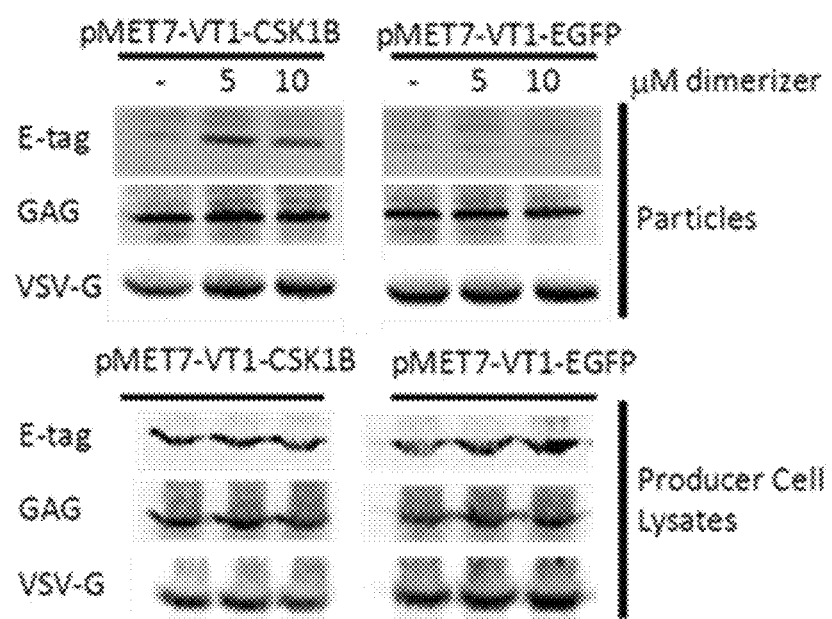
FIG. 3: Western blot showing the interaction between CSK1B bait and CDK2 prey upon addition of dimerizer (5 and 10 µM). HEK293T cells were transfected with the pMET7-VT1-CSK1B or pMET7-VT1-EGFP bait constructs, combined with the E-tagged CDK2 prey construct. After purification, the nanoparticles were directly brought in 2×SDS-PAGE loading buffer and loaded for SDS-PAGE separation and Western blot analysis. The three upper panels show samples prepared from purified particles. The lower panels are lysate samples obtained from the producer cells, confirming similar expression levels for the different components.

A well-described protein-protein interaction pair was used to test the conditional trapping in nanoparticles. The coding sequence for the CDC28 Protein Kinase Regulatory Subunit 1B (CKS1B) protein was fused to the FKBP12 in the VT1 vector. Addition of the chimeric dimerizer molecule, which consists of methotrexate (Mtx) and FK506 linked by a polyethylene glycol linker, would thus result in the recruitment of the CKS1B bait protein to the GAG protein and to the forming nanoparticles (FIG. 3). The pMET7-VT1-EGFP bait construct was also transfected as a control for irrelevant associations. The interaction partner Cyclin-Dependent Kinase 2 (CDK2), which has an N-terminal E-tag sequence, was co-expressed with both the CSK1B bait protein and the EGFP control protein. Three separate transfections were performed for each bait construct in combination with the CDK2 prey. The first series was left untreated to verify dimerizer-independent interactions, while the second and third series were treated with 5 and 10 µM of dimerizer, respectively. After enrichment and direct elution in SDS loading buffer, the samples were loaded on a 10% PAGE gel and transferred to nitrocellulose membranes after migration. The membranes were first probed with antibodies directed against the E-tag revealing presence of the prey protein in dimerizer-treated and bait-specific conditions. Expression of GAG and VSV-G was verified by using specific antibodies. The expression of the prey (E-tag), GAG and VSV-G was also monitored in the lysates from the producer cells to ensure equal protein levels.

Clear dimerizer-specific recruitment of the prey construct to the particles can be shown in case of co-expression of the bait CSK1B and prey CDK2. Some weak background association independent from the dimerizer is observed when the EGFP bait is expressed.

Example 5: Evaluation of the Viral Particle Trap

Figure 4:
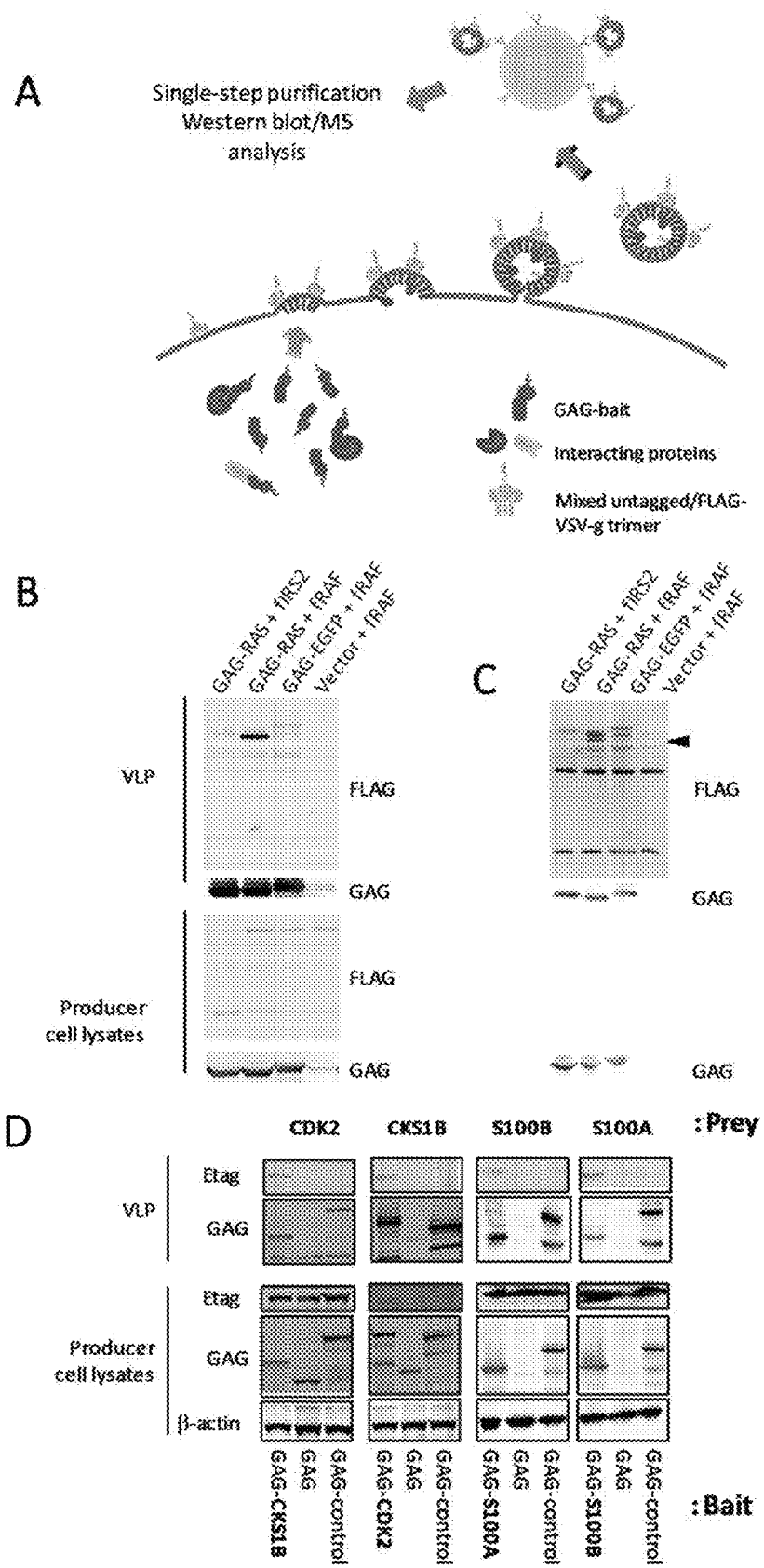
FIG. 4: Panel A: Schematic representation of the Virotrap strategy. Expression of a GAG-bait fusion protein results in the submembrane multimerization and consequent budding of virotrap particles from the cells. Interaction partners of the bait protein are also trapped in these virotrap particles and can be identified after purification and MS analysis. Panel B: Supernatants from HEK293T cells transfected with different combination of bait proteins (GAG-EGFP control and GAG-Ras) and FLAG-tagged prey proteins (IRS2 and RAF), were harvested after 24 hours, and were processed by ultracentrifugation to pellet the particles. Particle pellets were separated by SDS-PAGE and probed after Western blotting with anti-FLAG antibodies. Panel C: HEK293T cells were seeded in six-well plates and transfected with bait and prey combinations as in Panel B. Both wild-type and E-tagged VSV-G glycoproteins were expressed to allow particle enrichment via a single-step protocol from a 1 ml harvest. Western blotting of the eluted particles was performed with anti-FLAG and anti-GAG antibodies. Panel D: Virotrap experiments for two interaction pairs in both directions. Single-step purifications via anti-FLAG antibodies from six-well transfections were loaded for Western blotting and probed with anti-Etag, anti-GAG and anti-Actin antibodies for both the enriched particles and the producer cell lysates. The expression of GAG-S100A1 and GAG-S100B was below the detection limit in the lysates. Note that expression of the GAG protein without a fused bait does not lead to detectable particle formation.

To remove the homogenization step in classical AP-MS strategies, it was reasoned that incorporation of a protein complex inside a secreted vesicle should "trap" the interactions under native conditions and should protect the complex during the downstream purification process. As expression of the HIV1 p55 GAG protein allowed the formation of secreted particles, the concept of packaged or "wrapped" protein complexes was explored by the generation of a plasmid for the expression of GAG fused in frame to a bait protein. A flexible hinge sequence was inserted to limit sterical interference. FIG. 4, Panel A shows a schematic presentation of the Virotrap concept. The N-terminus of GAG is essential for membrane association through myristoylation and should thus remain available (Bryant and Ratner, 1990). All domains required for multimerization were still present in the expression construct. As a first PPI pair to evaluate the concept, the H-Ras protein that lacked the myristoylation signal as a bait was selected, combined with the cRAF prey protein. A GAG-EGFP construct and an IRS2 prey were used as irrelevant bait and prey, respectively. Both preys contained an N-terminal FLAG tag to facilitate detection. A first method of particle enrichment was ultracentrifugation, a well-described strategy for the concentration of lentiviral particles for various cell biological applications. After co-expression of bait and prey proteins, cell supernatants were harvested, filtered and centrifuged. After removal of the supernatant, the pelleted particles were resuspended directly in loading buffer and loaded for SDS-PAGE. After Western blotting and revelation of the tagged cRAF protein, clear enrichment of the prey protein could be demonstrated only when the H-Ras bait protein was present (FIG. 4, Panels B and C). Expression controls for the particles and the producer cell lysates showed comparable expression for all bait and prey constructs. These results showed that the interaction between H-Ras and cRAF can be detected by co-packaging of bait and prey in secreted particles from live cells. A "mock" empty vector for bait expression was also employed to exclude enrichment of the prey in exosomes that were also pelleted by the ultracentrifugation procedure.

To remove the tedious ultracentrifugation step, a single-step enrichment protocol for particles in the supernatant was developed and optimized. Briefly, co-expression of the classical VSV-G pseudotyping construct, together with a tagged variant of this glycoprotein, resulted in optimal presentation of the purification tag on the surface of the particles. Paramagnetic beads containing immune reagents for the affinity tag were then employed to capture the particles from the supernatant. First, the interaction between H-Ras and cRAF was confirmed using this new purification strategy. In this case, the system was based on the co-expression of untagged VSV-G with E-tagged VSV-G for capture and purification. HEK293T cells were transfected in a six-well format with GAG-RAS bait together with FLAG-RAF prey, and the controls used in the ultracentrifugation experiment. Virotrap particles were produced for 24 hours and were harvested in 1 ml of supernatant. After purification using anti-E antibodies coupled to paramagnetic particles, SDS-page and Western blotting, the preys were revealed using ANTI-FLAG® antibodies. Clear and specific enrichment of cRAF-prey was shown for the H-Ras-bait protein. No, or very little, cRAF was revealed in case of a-specific bait, while no detectable irrelevant IRS2-prey was found for the H-Ras-bait.

The interaction between two protein pairs in both directions was then explored. These protein interactions were selected based on literature evidence on their confirmation in independent methods (Braun et al., 2009), and because both protein partners reside in the cytoplasm. In this case, the purification strategy with a FLAG-tagged VSV-G variant was used to replace the E-tagged VSV-G glycoprotein in the previous experiment. After purification by the one-step protocol using ANTI-FLAG® resin, direct elution in PAGE loading buffer, and Western blotting for the E-tag, interactions between CDK2 and CKS1B and between S100A and S100B were readily detected. By swapping bait and prey, the interactions in both directions were shown (FIG. 4, Panel D). As controls, irrelevant bait and prey constructs were used.

Figure 5:
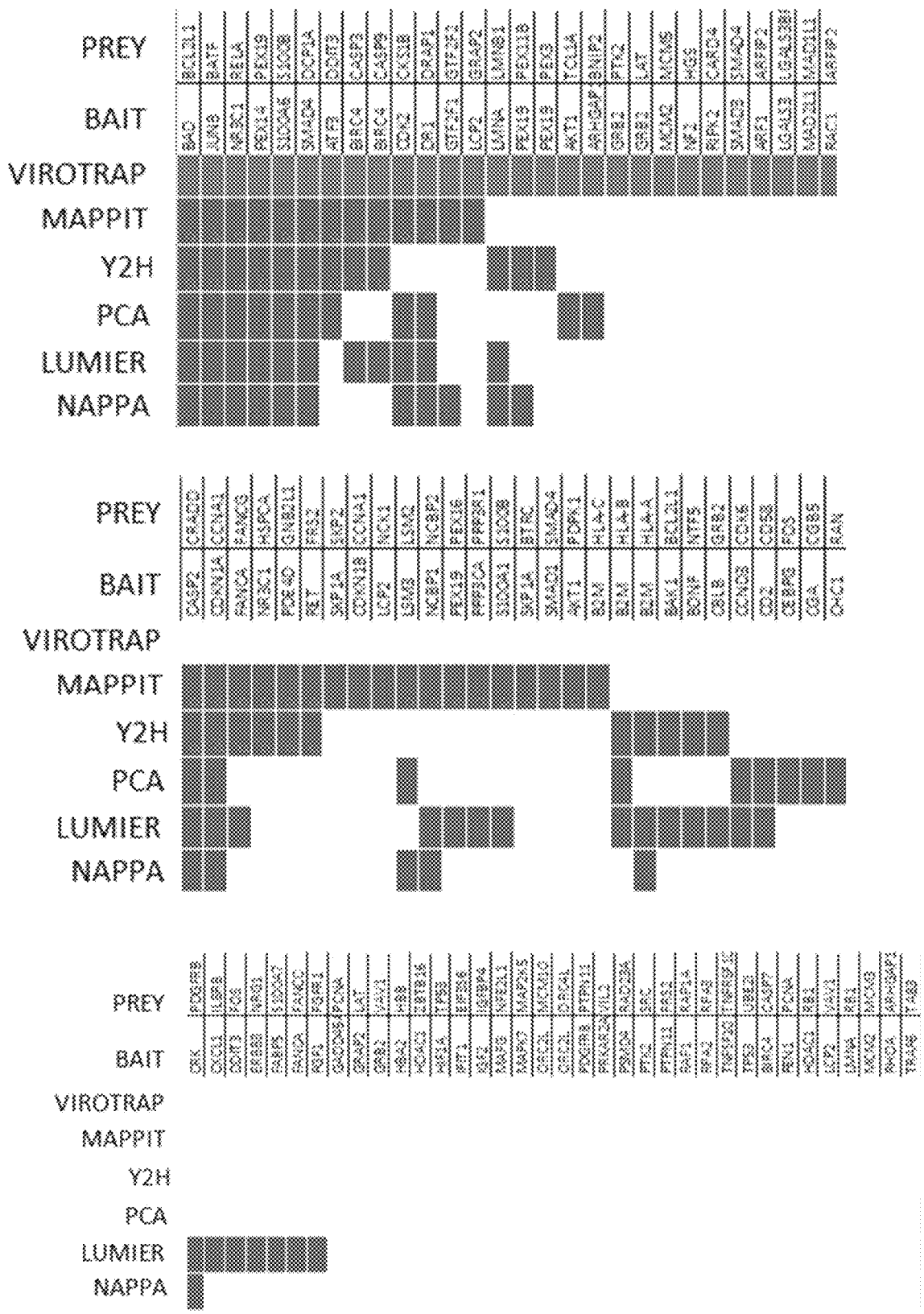
FIG. 5: Detection of binary interactions with Virotrap. Comparison of the results for the positive (PRS) and the random reference set (RRS) obtained with the Virotrap system with other binary systems. All interactions from the PRS and RRS were explored by transfection in six-well plates, processing by a single-step purification protocol, and Western blot analysis of the eluted particles and lysates of the producer cells. The presence of prey proteins was revealed by anti-Etag antibodies on the VLP samples. The colored blocks show the Virotrap results for 30% positive interactions at the expense of 5% false positive signals in the RRS set. For the other methods, data from Braun et al., 2009, was used.

By design, the Virotrap system is ideally suited to study cytoplasmic interactions. To explore the uses and limitations and to compare to other existing technologies, the concept was evaluated by testing the human positive reference set (hsPRS-v1). The positive reference set consists of 92 PPIs that were selected based on literature data, while the random reference set is generated using 188 randomly selected proteins (hsRRS-v1; (Venkatesan et al., 2009). Both sets contain proteins from all cellular compartments to remove any bias in localization. All PPIs from the PRS were tested in the Virotrap technology by recombination-assisted transfer of one bait set in fusion to the GAG protein. Prey ORFs were transferred to an expression vector resulting in N-terminally E-tagged fusion proteins. The PPIs were tested in a single direction implying no swap of bait and prey constructs. The same strategy was used for the RRS set, again without swapping of bait and prey proteins. All experiments were performed by transfection of bait and prey expression vectors in HEK293T cells in a six-well format. One day after transfection, supernatants were harvested and processed using the one-step purification protocol. Enriched particles were eluted from the paramagnetic beads in PAGE loading buffer and loaded on SDS-PAGE gels. A total of about 184 binary virotrap experiments were performed. Apart from positive and negative controls, the experiments were controlled for transfection and for immunoblotting efficiency. The presence of prey proteins in purified particles was revealed via anti-E tag immunoblots. The threshold of detection of true positives versus false positives was set for every individual gel. This led to the detection of 28 (31%) interactions in the PRS, while five (5%) interactions were detected in the RRS. Expression of the bait protein fusions in the lysates of the producer cells was verified, which showed that approximately 30% (56 out of 184 bait fusions) was not expressed at a detectable level. Although this could be explained by structural constraints in the fusion proteins or by interference with particle formation, only detectable expression was observed for 25 out of 41 tested prey proteins (61%) of the prey proteins in the producer lysates, where only an N-terminal E-tag was inserted before the protein. Therefore, it is believed that the current data provides an underestimate of the detectable interactions. FIG. 5 shows the overlap between the Virotrap data and data obtained with other PPI methods for the PRS and RRS as published by Braun and colleagues (2009). Seven interactions out of the positive reference set can be detected with all methods, while nine interactions are unique for the Virotrap method, proving the unique application window for the technology.

Example 6: Discovery of Novel Interaction Partners Using Co-complex Virotrap

For the detection of novel interaction partners, the purification procedure was scaled up to compensate for a larger production scale.

Figure 6:
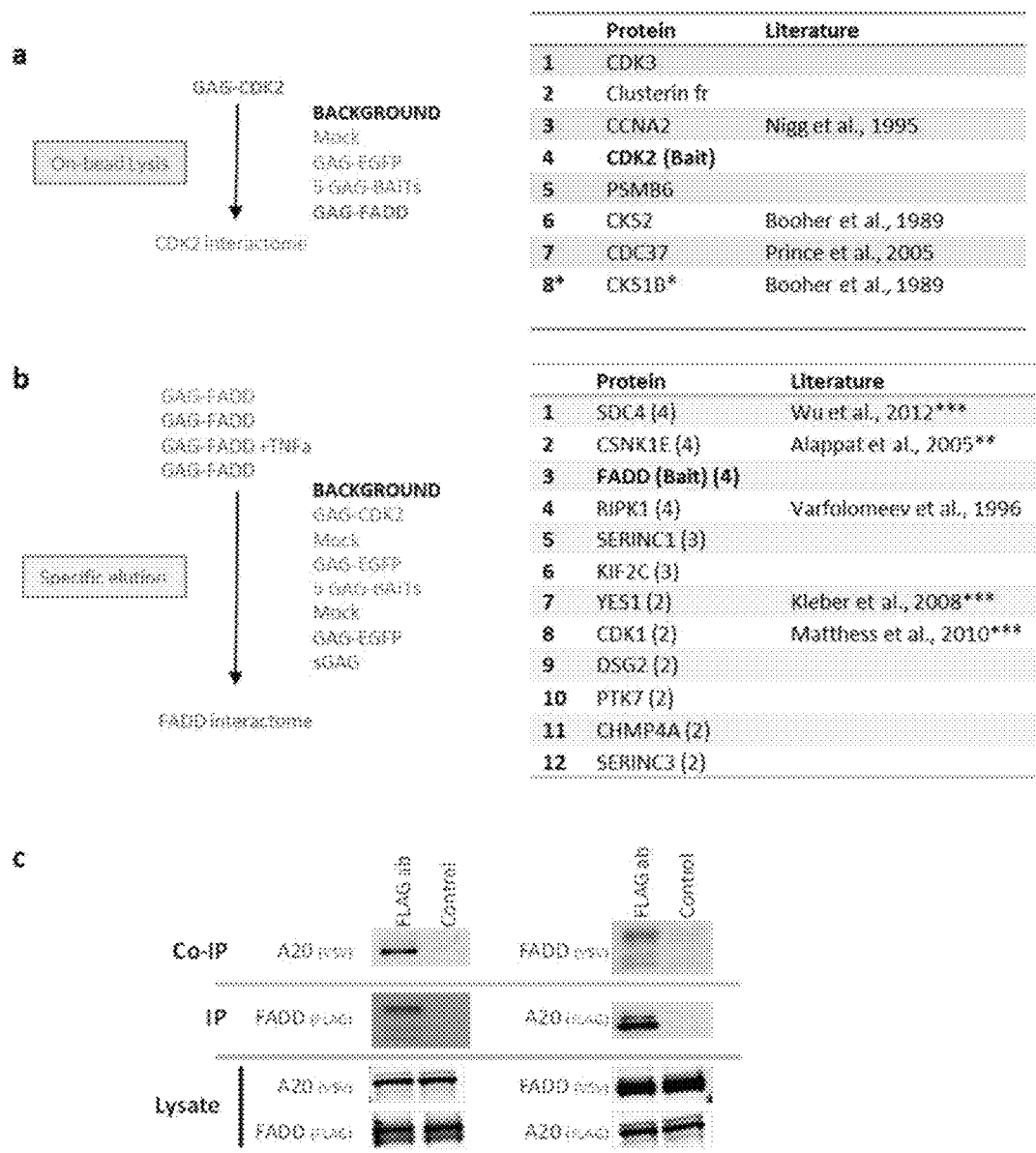
FIG. 6: Identification of novel interaction partners using co-complex MS analysis. Panel a: Analysis of the CDK2 interactome using Virotrap. A total of nine Virotrap experiments with on-bead VLP lysis was performed. The GAG-CDK2 identification list was challenged with identification lists from mock and GAG-EGFP controls, from GAG-FADD and from five additional Virotrap experiments. The CDK2 interactome (Right Panel Table) was obtained by removing all protein identifications found in the other experiments. *CKS1B was retained as it was also used as a GAG-BAIT construct in the reference experiments. Note that the CDK2-CKS1B interaction is a model interaction used for validation of the system. Panel b: The FADD interactome was obtained by adding three repeat experiments and controls using a specific elution protocol (scheme on the left). One of the FADD repeats was treated with TNFα during production. The protein list (right panel table) was obtained by considering only confident identifications (at least two peptides) and by removing all proteins identified in the eleven other experiments. The numbers in brackets show the number of times the protein was identified in the four FADD experiments. *: interaction was shown with Casein Kinase 1 α(CSNK1A). **Affects FAS signaling. Panel c: Confirmation of the A20-FADD interaction. A20 was found in two FADD Virotrap experiments. The interaction was confirmed by co-immunoprecipitation experiments showing specific binding of A20 to immune-precipitated FADD (left panels), or of FADD to immune-precipitated A20 (right panels). Tagged proteins (FLAG and VSV tags) were expressed in HEK293T cells and were precipitated after lysis using paramagnetic anti-FLAG beads. The co-precipitated proteins were revealed by anti-VSV antibodies.

The protein complexes of two cytosolic proteins were investigated in more detail: Cyclin-Dependent Kinase 2 (CDK2) and Fas-Associated via Death Domain (FADD). An important issue in typical MS co-complex strategies relates to the background. The background in Virotrap will contain GAG- and VSV-G-derived peptide sequences, together with host binding partners, proteins implicated in budding, and serum proteins associated with the outside of the VLPs. To define these background proteins, additional experiments in the design of this study were included to allow the construction of a comprehensive background list. In its simplest format, this list can be subtracted from the protein identifications that are specific for the bait (FIG. 6, Panel a). A total of nine experiments were performed (mock control, EGFP bait and five additional bait constructs). Cells were co-transfected with bait proteins and constructs for purification. After harvest and purification, particles were lysed directly on the beads using a chaotropic lysis buffer. The lysates were then processed by reduction and alkylation, buffer exchange and trypsin digest. MS analysis followed by identification via MASCOT (99% confidence) resulted in the identification of between 140 (for LCP2 bait) to 277 (FADD) proteins by at least two unique peptides (Table 2). By comparing the identification lists, a background list of 306 proteins that were found in at least two of the lists were extracted for the different experiments (Table 3). By subtraction of this list from the CDK2 identification list, a limited set of 15 putative binding partners remains. Further removal of protein identifications that were also found with a single peptide in other experiments revealed a short list of seven binding partners. For four of these candidates, there is clear evidence in literature (FIG. 6, Panel a). The list of unique proteins for FADD is more extensive (73 proteins), even after removal of proteins that were additionally found in one of the other experiments with a single peptide (35 proteins, Table 4). It is clear that this list contains real binding partners (Receptor interacting protein 1 RIPK1, Casein Kinase 1 alpha and epsilon) as well as unlikely binders. Therefore, the analysis of FADD using additional Virotrap experiments was extended by using a specific elution protocol. In these experiments, the particles from the FLAG-antibody beads were eluted by competition with FLAG-peptide. The particles were then lysed in SDS, processed with detergent removal columns, and digested by trypsin. Controls included in these experiments were mock, EGFP bait and an expression construct of a GAG variant without a bait. Three additional experiments for the FADD interactome were performed (FIG. 6, Panel b, Table 5 for overview). Combination of the identifications from these experiments and the previous nine Virotrap assays resulted in a specific list of three candidate partners identified uniquely with at least two peptides in all four FADD experiments: Syndecan 4 (SDC4), Casein kinase 1 epsilon (CSNK1E) and RIPK1. The list of candidate partners identified in two out of four experiments also contained two additional kinases: YES1 and Cyclin-Dependent Kinase 1 (CDK1) (FIG. 6, Panel b, right side table).

Relaxing the criteria where all identifications (including single peptide identifications) in fewer of the repeat samples were included, revealed FAS receptor as candidate interaction partner in the lists of identifications, while TRADD was also found in a single FADD experiment. A20 (TNFAIP3) was identified in the first experiment series, and could be confirmed upon treatment of the cells with TNFα during Virotrap particle production. The interaction between FADD and A20 was also shown by orthogonal co-immunoprecipitation (Co-IP) experiments (FIG. 6, Panel c).

TABLE 2

Overview of the proteomics data obtained for different GAG-bait constructs.

| | PRIDE Experiment Accession | # Spectra | # Peptide sequences | # Proteins (all) | # Proteins (>1 peptide) | # Unique proteins (>1 peptide) | FDR (%) |
|---|---|---|---|---|---|---|---|
| Mock | 28956 | 7529 | 1093 | 297 | 158 | 6 | 0.4 |
| GAG-EGFP | 28955 | 8142 | 1253 | 368 | 193 | 17 | 0.4 |
| GAG-CDK2 | 28954 | 7618 | 1237 | 360 | 195 | 16 | 0.3 |
| GAG-FADD | 28959 | 6752 | 1889 | 463 | 277 | 73 | 0.7 |
| GAG-TRAF3 | 28958 | 5461 | 1411 | 329 | 173 | 11 | 0.7 |
| GAG-CKS1B | 28953 | 7486 | 1246 | 374 | 218 | 33 | 0.4 |
| GAG-LCP2 | 28951 | 7728 | 1264 | 260 | 140 | 9 | 0.4 |
| GAG-GRAP2 | 28952 | 6768 | 1197 | 340 | 189 | 7 | 0.4 |
| GAG-S100A | 28957 | 6399 | 1361 | 311 | 184 | 21 | 0.3 |

Results were obtained by searches of MS/MS data against all human and bovine SWISSPROT accessions, complemented with HIV-1, EGFP and VSV-G sequences by using MASCOT ® software. False discovery rates (FDRs) were determined by MASCOT ® searches against a database containing all sequences after reversion. Numbers are shown for all identified proteins (all) or proteins identified with at least two peptides (>1 peptide). Unique proteins were obtained by only considering protein identifications with at least two peptides after removal of proteins that were identified in one of the other Virotrap experiments.

TABLE 3

List of background proteins that were found in at least two out of nine Virotrap experiments. Both SWISSPROT accessions and gene names are shown, as well as the number of Virotrap experiments containing the protein (x/9).

| accession | Gene symbol | Times identified |
|---|---|---|
| A5A3E0 | POTEF | 9 |
| A5PJE3 | FGA | 9 |
| E1B7N2 | LOC619094 | 9 |
| E1B8G9 | HIST3H2BB | 9 |
| E1B953 | TUBB | 9 |
| E1B9F6 | LOC100848359 | 9 |
| E1B9K1 | UBC | 9 |
| E1BH06 | LOC617696 | 9 |
| E1BJB1 | TUBB2A | 9 |
| F1MI18 | LOC506828 | 9 |
| F1MNF8 | LOC100141266 | 9 |
| F1MNW4 | ITIH2 | 9 |
| F1MRD0 | ACTB | 9 |
| F1MSZ6 | SERPINC1 | 9 |
| F1MYN5 | FBLN1 | 9 |
| F1N5M2 | GC | 9 |
| G3N2V5 | HSP90AB1 | 9 |
| G3X6N3 | TF | 9 |
| G5E513 | Bt.12809 | 9 |
| O00560 | SDCBP | 9 |
| O46375 | TTR | 9 |
| P00735 | F2 | 9 |
| P01966 | HBA | 9 |
| P02081 | HBBF_BOVIN Hemoglobin fetal subunit beta OS = Bos taurus PE = 1 SV = 1 | 9 |
| P02769 | ALB | 9 |
| P07437 | TUBB | 9 |
| P07900 | HSP90AA1 | 9 |
| P08107 | HSPA1A | 9 |
| P08670 | VIM | 9 |
| P11142 | HSPA8 | 9 |
| P12268 | IMPDH2 | 9 |

TABLE 3-continued

List of background proteins that were found in at least two out of nine Virotrap experiments. Both SWISSPROT accessions and gene names are shown, as well as the number of Virotrap experiments containing the protein (x/9).

| accession | Gene symbol | Times identified |
|---|---|---|
| P12763 | AHSG | 9 |
| P15497 | APOA1 | 9 |
| P22626 | HNRNPA2B1 | 9 |
| P28800 | SERPINF2 | 9 |
| P34955 | SERPINA1 | 9 |
| P35580 | MYH10 | 9 |
| P56652 | ITIH3 | 9 |
| P81187 | CFB | 9 |
| P81644 | APOA2 | 9 |
| Q00839 | HNRNPU | 9 |
| Q03247 | APOE | 9 |
| Q07020 | RPL18 | 9 |
| Q08431 | MFGE8 | 9 |
| Q13813 | SPTAN1 | 9 |
| Q3SZ57 | AFP | 9 |
| Q3SZR3 | ORM1 | 9 |
| Q3ZBS7 | VTN | 9 |
| Q58D62 | FETUB | 9 |
| Q7SIH1 | A2M | 9 |
| Q9BQA1 | WDR77 | 9 |
| A2I7M9 | SERPINA3-2 | 8 |
| F1MGU7 | FGG | 8 |
| F1MMK9 | AMBP | 8 |
| Q29443 | TF | 8 |
| Q2KJF1 | A1BG | 8 |
| Q3SZV7 | HPX | 8 |
| F1MBQ8 | DDX5 | 8 |
| F2Z4C1 | TUBA3C | 8 |
| G5E507 | HSP90AB1 | 8 |
| P17697 | CLU | 8 |
| P35527 | KRT9 | 8 |
| P60709 | ACTB | 8 |
| Q3SYW6 | EIF3C | 8 |
| A1A4R1 | HIST2H2AC | 8 |
| P01045 | KNG2 | 8 |
| P26373 | RPL13 | 8 |
| 12831136 | gb\|AAK08483.1\|AF324493_2 gag polyprotein [HIV-1 vector pNL4-3] | 8 |
| A6NKZ8 | YI016_HUMAN Putative tubulin beta chain-like protein ENSP00000290377 OS = *Homo sapiens* PE = 5 SV = 2 | 8 |
| Q28107 | F5 | 8 |
| P04264 | KRT1 | 8 |
| P13645 | KRT10 | 8 |
| A6QLG5 | RPS9 | 8 |
| A7E350 | PLG | 8 |
| E1BEG2 | HNRNPA3 | 8 |
| G8JKY0 | RPS8 | 8 |
| P15311 | EZR | 8 |
| P39023 | RPL3 | 8 |
| P62424 | RPL7A | 8 |
| A2I7N3 | SERPINA3-7 | 7 |
| A7E307 | DDX17 | 7 |
| F1MJH1 | GSN | 7 |
| F1MY44 | HNRNPM | 7 |
| G1K122 | RBP4 | 7 |
| O43175 | PHGDH | 7 |
| P00003 | FLAG-VSVG | 7 |
| P12259 | F5 | 7 |
| P61978 | HNRNPK | 7 |
| Q9TTJ5 | RGN | 7 |
| Q3Y5Z3 | ADIPOQ | 7 |
| E1BF20 | HNRNPH1 | 7 |
| G5E5T5 | G5E5T5_BOVIN Uncharacterized protein (Fragment) OS = *Bos taurus* PE = 4 SV = 1 | 7 |
| 296556483 | gb\|AAK08484.2\|AF324493_3 pol polyprotein [HIV-1 vector pNL4-3] | 7 |
| E1B7J1 | E1B7J1_BOVIN Elongation factor 1-alpha OS = *Bos taurus* PE = 3 SV = 1 | 7 |
| E1BAK6 | DAZAP1 | 7 |
| F1MWU9 | HSPA6 | 7 |
| P40429 | RPL13A | 7 |
| A5D9B4 | HNRPH2 | 7 |
| E1BHA5 | E1BHA5_BOVIN Uncharacterized protein OS = *Bos taurus* PE = 4 SV = 1 | 7 |
| P09651 | HNRNPA1 | 7 |
| P11940 | PABPC1 | 7 |
| P61353 | RPL27 | 7 |
| A2VE06 | RPS4Y1 | 7 |
| G3N262 | G3N262_BOVIN Uncharacterized protein OS = *Bos taurus* PE = 3 SV = 1 | 7 |
| P62269 | RPS18 | 7 |
| P26038 | MSN | 7 |
| A7YW45 | PRMT5 | 6 |
| G3MYZ3 | AFM | 6 |
| Q05443 | LUM | 6 |
| F1MY85 | C5 | 6 |
| A6NHL2 | TUBAL3 | 6 |
| P60842 | EIF4A1 | 6 |
| F1MQ37 | MYH9 | 6 |
| A6QPP2 | SERPIND1 | 6 |
| P35579 | MYH9 | 6 |
| P35908 | KRT2 | 6 |
| P29966 | MARCKS | 6 |
| E1B7R4 | EIF3A | 6 |
| P13639 | EEF2 | 6 |
| P12277 | CKB | 6 |
| P23528 | CFL1 | 6 |
| E1B8G4 | E1B8G4_BOVIN Uncharacterized protein OS = *Bos taurus* PE = 3 SV = 2 | 6 |
| P62917 | RPL8 | 6 |
| Q8IX12 | CCAR1 | 6 |
| P04406 | GAPDH | 6 |
| P14618 | PKM | 6 |
| Q0VCZ3 | YTHDF2 | 6 |
| G3MX91 | TARDBP | 6 |
| F1MI47 | RBM14 | 5 |
| A5D784 | CPNE8 | 5 |
| G3N0S9 | LOC515150 | 5 |
| F1MNV5 | KNG1 | 5 |
| Q2UVX4 | C3 | 5 |
| A5PK20 | HIST1H1E | 5 |
| F1MYC9 | SPTBN1 | 5 |
| F1MVC0 | CAD | 5 |
| E1BGR6 | E1BGR6_BOVIN Uncharacterized protein OS = *Bos taurus* PE = 3 SV = 1 | 5 |
| P62249 | RPS16 | 5 |
| P83731 | RPL24 | 5 |
| G3X861 | G3X861_BOVIN Uncharacterized protein (Fragment) OS = *Bos taurus* PE = 3 SV = 1 | 5 |
| P62280 | RPS11 | 5 |
| P08865 | RPSA | 5 |
| A5PKD6 | GNB4 | 5 |
| F1MKC4 | F1MKC4_BOVIN Uncharacterized protein OS = *Bos taurus* PE = 3 SV = 2 | 5 |
| P26641 | EEF1G | 5 |
| Q06830 | PRDX1 | 5 |
| P09543 | CNP | 5 |
| F1MMD7 | ITIH4 | 5 |
| Q3T052 | ITIH4 | 4 |
| P02768 | ALB | 4 |
| P55884 | EIF3B | 4 |
| P02538 | KRT6A | 4 |
| A7MAZ5 | HIST1H1D | 4 |
| P35613 | BSG | 4 |
| Q3SZH5 | AGT | 4 |
| P39060 | COL18A1 | 4 |
| P60033 | CD81 | 4 |
| P62937 | PPIA | 4 |
| Q01082 | SPTBN1 | 4 |
| Q08E32 | CHMP4B | 4 |
| A5PK61 | H3F3C | 4 |
| Q13151 | HNRNPA0 | 4 |
| F1MB60 | RPS26 | 4 |

TABLE 3-continued

List of background proteins that were found in at least two out of nine Virotrap experiments. Both SWISSPROT accessions and gene names are shown, as well as the number of Virotrap experiments containing the protein (x/9).

| accession | Gene symbol | Times identified |
|---|---|---|
| P23396 | RPS3 | 4 |
| F1MMP5 | ITIH1 | 4 |
| O15372 | EIF3H | 4 |
| P46777 | RPL5 | 4 |
| Q02543 | RPL18A | 4 |
| G3X7A5 | C3 | 4 |
| E1BE42 | E1BE42__BOVIN Uncharacterized protein OS = Bos taurus PE = 3 SV = 1 | 4 |
| Q9Y265 | RUVBL1 | 4 |
| O18789 | RPS2 | 4 |
| G3N2F0 | G3N2F0__BOVIN Elongation factor 1-alpha OS = Bos taurus PE = 3 SV = 1 | 4 |
| P62913 | RPL11 | 4 |
| A6NMY6 | ANXA2P2 | 4 |
| E1BB17 | HNRNPH3 | 4 |
| P08779 | KRT16 | 4 |
| F6QVC9 | ANXA5 | 4 |
| E1BNB4 | PABPC1L | 4 |
| A6H769 | RPS7 | 4 |
| E1BAT6 | E1BAT6__BOVIN Uncharacterized protein OS = Bos taurus PE = 3 SV = 1 | 4 |
| Q562R1 | ACTBL2 | 4 |
| Q8WUM4 | PDCD6IP | 4 |
| P19338 | NCL | 3 |
| Q3SYR0 | SERPINA7 | 3 |
| P01614 | KV201__HUMAN Ig kappa chain V-II region Cum OS = Homo sapiens PE = 1 SV = 1 | 3 |
| P17690 | APOH | 3 |
| G3N361 | NONO | 3 |
| P63243 | GNB2L1 | 3 |
| P84103 | SRSF3 | 3 |
| Q01130 | SRSF2 | 3 |
| G8JKV5 | RPL14 | 3 |
| F1MJM0 | ZNF326 | 3 |
| F1ML72 | RPL34 | 3 |
| F1MSD2 | RUVBL2 | 3 |
| O15371 | EIF3D | 3 |
| P08621 | SNRNP70 | 3 |
| P18621 | RPL17 | 3 |
| G3X8B1 | LOC613401 | 3 |
| P62935 | PPIA | 3 |
| O43242 | PSMD3 | 3 |
| P41252 | IARS | 3 |
| P49327 | FASN | 3 |
| Q3MHL4 | AHCY | 3 |
| Q86YQ8 | CPNE8 | 3 |
| G5E604 | G5E604__BOVIN Uncharacterized protein (Fragment) OS = Bos taurus PE = 4 SV = 1 | 3 |
| Q12906 | ILF3 | 3 |
| A7MB16 | EIF3B | 3 |
| F1MH40 | Bt.57604 | 3 |
| E1BCL3 | LOC507211 | 3 |
| P54727 | RAD23B | 3 |
| G3N2D7 | IGLL1 | 3 |
| A7MBG8 | RUVBL1 | 3 |
| F1MZ00 | SNRPD3 | 3 |
| F1N6C0 | F1N6C0__BOVIN Uncharacterized protein OS = Bos taurus PE = 4 SV = 2 | 3 |
| Q13310 | PABPC4 | 3 |
| F1MXE4 | PSMD6 | 3 |
| A4IFP7 | ARF5 | 3 |
| F1N0E5 | CCT4 | 3 |
| P46779 | RPL28 | 3 |
| A5PK39 | TPP2 | 3 |
| P78371 | CCT2 | 3 |
| P02786 | TFRC | 3 |
| F1MPU0 | CLTC | 3 |
| O14744 | PRMT5 | 3 |
| Q969P0 | IGSF8 | 3 |
| Q9P2B2 | PTGFRN | 3 |
| P07224 | PROS1 | 2 |
| Q28085 | CFH | 2 |
| F1MG05 | EEF1G | 2 |
| F1MLW8 | LOC100847119 | 2 |
| E1BMJ0 | LOC100847889 | 2 |
| A0JND2 | KRT80 | 2 |
| B8Y9S9 | FN1 | 2 |
| P02656 | APOC3 | 2 |
| Q3MHN2 | C9 | 2 |
| F6QYV9 | SSRP1 | 2 |
| P02253 | HIST1H1C | 2 |
| P07910 | HNRNPC | 2 |
| P08758 | ANXA5 | 2 |
| P43243 | MATR3 | 2 |
| Q9Y2W1 | THRAP3 | 2 |
| E1BQ37 | SFPQ | 2 |
| P11586 | MTHFD1 | 2 |
| A6QLT5 | UBAP2L | 2 |
| E1B9M9 | LOC525863 | 2 |
| P20645 | M6PR | 2 |
| Q96EP5 | DAZAP1 | 2 |
| P40227 | CCT6A | 2 |
| P61024 | CKS1B | 2 |
| G1K134 | Bt.57435 | 2 |
| P84090 | ERH | 2 |
| P30101 | PDIA3 | 2 |
| F1MZ92 | YBX1 | 2 |
| A4IFC3 | PABPC4 | 2 |
| A5PK63 | RPS17 | 2 |
| E1BCF5 | RPL26L1 | 2 |
| F1MHJ6 | F1MHJ6__BOVIN 60S ribosomal protein L18a OS = Bos taurus PE = 3 SV = 2 | 2 |
| F1MLH6 | CALM2 | 2 |
| P05543 | SERPINA7 | 2 |
| P13010 | XRCC5 | 2 |
| Q15366 | PCBP2 | 2 |
| E1BF81 | SERPINA6 | 2 |
| P16403 | HIST1H1C | 2 |
| G5E531 | TCP1 | 2 |
| P02788 | LTF | 2 |
| P08238 | HSP90AB1 | 2 |
| P62194 | PSMC5 | 2 |
| P04350 | TUBB4A | 2 |
| P02533 | KRT14 | 2 |
| Q5D862 | FLG2 | 2 |
| D3IVZ2 | DDX3Y | 2 |
| O75131 | CPNE3 | 2 |
| P57721 | PCBP3 | 2 |
| Q5VW32 | BROX | 2 |
| E1BKM4 | PDCD6IP | 2 |
| P60660 | MYL6 | 2 |
| F1MZV2 | CHMP5 | 2 |
| O75340 | PDCD6 | 2 |
| P29144 | TPP2 | 2 |
| A5D9H5 | HNRPD | 2 |
| A6NIZ1 | RP1BL__HUMAN Ras-related protein Rap-1b-like protein OS = Homo sapiens PE = 2 SV = 1 | 2 |
| A7Z057 | YWHAG | 2 |
| E1B726 | PLG | 2 |
| E1B7T4 | E1B7T4__BOVIN Uncharacterized protein OS = Bos taurus PE = 3 SV = 2 | 2 |
| E1BK63 | E1BK63__BOVIN Ribosomal protein L15 OS = Bos taurus PE = 3 SV = 1 | 2 |
| E1BNR0 | Bt.110587 | 2 |
| G3MYE2 | G3MYE2__BOVIN Uncharacterized protein (Fragment) OS = Bos taurus PE = 3 SV = 1 | 2 |
| O14828 | SCAMP3 | 2 |
| P00004 | VSVG | 2 |
| P05023 | ATP1A1 | 2 |
| P06733 | ENO1 | 2 |
| P08195 | SLC3A2 | 2 |
| P18124 | RPL7 | 2 |
| P27635 | RPL10 | 2 |
| P36578 | RPL4 | 2 |

TABLE 3-continued

List of background proteins that were found in at least two out of nine Virotrap experiments. Both SWISSPROT accessions and gene names are shown, as well as the number of Virotrap experiments containing the protein (x/9).

| accession | Gene symbol | Times identified |
|---|---|---|
| P49006 | MARCKSL1 | 2 |
| P52272 | HNRNPM | 2 |
| P53985 | SLC16A1 | 2 |
| P61204 | ARF3 | 2 |
| P62258 | YWHAE | 2 |
| P62847 | RPS24 | 2 |
| Q02878 | RPL6 | 2 |
| Q14152 | EIF3A | 2 |
| Q15758 | SLC1A5 | 2 |
| Q53EZ4 | CEP55 | 2 |

TABLE 4

List of FADD interaction partners.

| | Accession | Protein |
|---|---|---|
| 1 | A2VDY3 | CHMP4A |
| 2 | A4FUC2 | HNRNPUL1 |
| 3 | A6QLS9 | RAB10 |
| 4 | E1BAF6 | PRRC2A |
| 5 | F1MND1 | CDC42 |
| 6 | F1MSI2 | AGRN |
| 7 | F1MX61 | SF3B1 |
| 8 | G3N3Q3 | G3N3Q3_BOVIN |
| 9 | G5E5V7 | G5E5V7_BOVIN |
| 10 | O00232 | PSMD12 |
| 11 | O00299 | CLIC1 |
| 12 | O60884 | DNAJA2 |
| 13 | P01891 | HLA-A |
| 14 | P05556 | ITGB1 |
| 15 | P06493 | CDK1 |
| 16 | P07195 | LDHB |
| 17 | P11017 | GNB2 |
| 18 | P21580 | TNFAIP3 |
| 19 | P31431 | SDC4 |
| 20 | P31689 | DNAJA1 |
| 21 | P48643 | CCT5 |
| 22 | P48729 | CSNK1A1 |
| 23 | P49674 | CSNK1E |
| 24 | P60174 | TPI1 |
| 25 | P61247 | RPS3A |
| 26 | P62871 | GNB1 |
| 27 | P62888 | RPL30 |
| 28 | Q13158 | FADD |
| 29 | Q13546 | RIPK1 |
| 30 | Q148F1 | CFL2 |
| 31 | Q8TB73 | NDNF |
| 32 | Q99661 | KIF2C |
| 33 | Q9NRX5 | SERINC1 |
| 34 | Q9UN37 | VPS4A |
| 35 | Q9Y5K6 | CD2AP |

List of FADD interaction partners after removal of all proteins (including single peptide protein identifications) that were found in at least one of the other Virotrap experiments. Proteins in bold have been linked to FADD or to FAS signaling before.

TABLE 5

Overview of the proteomics data obtained for different GAG-bait constructs using specific elution of particles from the purification beads.

| | PRIDE Experiment Accession | # Spectra | # Peptide sequences | # Proteins (all) | # Proteins (>1 peptide) | # Unique proteins (>1 peptide) | FDR (%) |
|---|---|---|---|---|---|---|---|
| mock | 28963 | 6706 | 557 | 169 | 95 | 14 | 0.6 |
| sGAG* | 28965 | 7661 | 595 | 255 | 117 | 18 | 0.4 |
| GAG-EGFP | 28964 | 6450 | 397 | 242 | 114 | 29 | 1.7 |
| GAG-FADD | 28962 | 7546 | 864 | 375 | 174 | 20 | 0.7 |
| GAG-FADD | 28960 | 8377 | 517 | 166 | 98 | 2 | 0.4 |
| GAG-FADD** | 28961 | 8388 | 717 | 231 | 121 | 9 | 0.5 |

Results were obtained by searches of MS data against all human and bovine SWISSPROT accessions, complemented with HIV-1, EGFP and VSV-G sequences. False discovery rates (FDRs) were determined by MASCOT searches against a database containing all sequences after inversion.
*an alternative codon-optimized GAG construct without a bait was used to generate particles.
**GAG-FADD Virotrap particles were produced in the presence of TNFα.

Example 7: Identification of Desmosomal Components

By employing a similar background removal strategy for the S100A1 bait as for the CDK2 bait (i.e., removal of all a-specific proteins identified) in the first set of nine experiments, a list of ten putative interaction partners identified with at least two peptides was obtained (Table 6). Remarkably, three components of the desmosome can be found in this list (Desmoplakin DSP, Desmoglein 1 DSG1 and Junction Plakoglobin JUP), as well as two keratin proteins not found in other bait proteins (thus, not constituting classical contaminating keratins). These keratins are known intermediate filament components that use the desmosome for anchoring (Kitajima, 2013). The link between S100 proteins and desmosomes is hinted in literature. The S100A10 and S100A11 can be found together with desmosomal proteins in the cornified envelope (Robinson et al., 1997). Various members of the S100 family of proteins have been implicated in inflammatory skin disorders affecting the integrity of the skin such as psoriasis (Eckert et al., 2004). In addition, it is clear that these calcium-binding proteins play an important role in metastasis of tumors, both in the primary tumor cells and the metastatic niche (Lukanidin and Sleeman, 2012). The S100A1 protein also plays an important role in striated muscle and has been implicated in myocardial (dys)function and heart failure (Krause et al., 2009).

FIG. 7 shows the mapping of the identified peptides of Desmoglein 1 on the amino acid sequence. Peptides from both the extracellular part and the intracellular part of the protein were identified. In Table 7, the identified peptides for Desmoglein 1 are shown with their MASCOT scores. This data clearly supports the fact that Virotrap allows the detection of transmembrane prey proteins.

TABLE 6

Putative interaction partners for the S100A1 bait protein. Desmosomal or intermediate filament proteins are annotated in the comments column.

| Accession | Protein | Comment |
|---|---|---|
| P05089 | ARG1 | |
| P13647 | KRT5 | Intermediate filament |
| P14923 | JUP | Desmosome component |
| P15924 | DSP | Desmosome component |
| P23297 | S100A1 | BAIT |
| Q02413 | DSG1 | Desmosome component |
| Q6UWP8 | SBSN | |
| Q8N1N4 | KRT78 | Intermediary filament |
| Q96P63 | SERPINB12 | |
| Q99816 | TSG101 | |
| Q9UK41 | VPS28 | |

TABLE 7 the identified peptides for Desmoglein 1 (DSG1, Swissprot Accession Q02413) are shown with their respective MASCOT ® scores.

| Peptide | start aa position | end aa position | modified peptide sequence | MASCOT ® score | SEQ ID NO |
|---|---|---|---|---|---|
| I | 439 | 445 | NH2-TGKLTLK-COOH | 33 | 13 |
| E | 916 | 925 | NH2-ESSNVVVTER-COOH | 77 | 14 |
| J1 | 326 | 332 | NH2-TNVGILK-COOH | 41 | 15 |
| F | 198 | 213 | NH2-IIRQEPSDSPM(oxid)FIINR-COOH | 57 | 16 |
| A | 129 | 144 | NH2-ALNSMGQDLERPLELR-COOH | 48 | 17 |
| M + K | 391 | 422 | NH2-TYVVTGNMGSNDKVGDFVATDLDTGRPSTTVR-COOH | 84 | 18 |
| F | 198 | 213 | NH2-IIRQEPSDSPMFIINR-COOH | 74 | 19 |
| D | 220 | 238 | NH2-TM(oxid)NNFLDREQYGQYALAVR-COOH | 73 | 20 |
| L | 423 | 438 | NH2-YVMGNNPADLLAVDSR-COOH | 107 | 21 |
| D | 220 | 238 | NH2-TMNNFLDREQYGQYALAVR-COOH | 75 | 22 |
| J2 | 333 | 352 | NH2-VVKPLDYEAMQSLQLSIGVR-COOH | 49 | 23 |
| G | 87 | 105 | NH2-ISGVGIDQPPYGIFVINQK-COOH | 118 | 24 |
| B | 369 | 390 | NH2-ASAISVTVLNVIEGPVFRPGSK-COOH | 86 | 25 |

REFERENCES

Booher R. N., C. E. Alfa, J. S. Hyams, and D. H. Beach (1989). The fission yeast cdc2/cdc13/suc1 protein kinase: regulation of catalytic activity and nuclear localization. *Cell* 58:485-497.

Braun P., M. Tasan, M. Dreze, M. Barrios-Rodiles, I. Lemmens, H. Yu, J. M. Sahalie, R. R. Murray, L. Roncari, and A. S. de Smet, et al. (2009). An experimentally derived confidence score for binary protein-protein interactions. *Nat. Methods* 6:91-97.

Briggs J. A., M. N. Simon, I. Gross, H. G. Krausslich, S. D. Fuller, V. M. Vogt, and M. C. Johnson (2004). The stoichiometry of Gag protein in HIV-1. *Nat. Struct. Mol. Biol.* 11:672-675.

Bryant M. and L. Ratner (1990). Myristoylation-dependent replication and assembly of human immunodeficiency virus 1. *Proc. Natl. Acad. Sci. U.S.A.* 87:523-527.

Caligiuri M., L. Molz, Q. Liu, F. Kaplan, J. P. Xu, J. Z. Majeti, R. Ramos-Kelsey, K. Murthi, S. Lievens, and J. Tavernier, et al. (2006). MASPIT: three-hybrid trap for quantitative proteome fingerprinting of small molecule-protein interactions in mammalian cells. *Chem. Biol.* 13:711-722.

Eyckerman S., I. Lemmens, D. Catteeuw, A. Verhee, J. Vandekerckhove, S. Lievens, and J. Tavernier (2005). Reverse MAPPIT: screening for protein-protein interaction modifiers in mammalian cells. *Nat. Methods* 2:427-433.

Eyckerman S., A. Verhee, J. V. der Heyden, I. Lemmens, X. V. Ostade, J. Vandekerckhove, and J. Tavernier (2001). Design and application of a cytokine-receptor-based interaction trap. *Nat. Cell. Biol.* 3:1114-1119.

Eckert R. L., A. M. Broome, M. Ruse, N. Robinson, D. Ryan and K. Lee (2004). S100 proteins in the epidermis. *J. Invest. Dermatol.* 123:23-33.

Gavin A. C., M. Bosche, R. Krause, P. Grandi, M. Marzioch, A. Bauer, J. Schultz, J. M. Rick, A. M. Michon, and C. M. Cruciat, et al. (2002). Functional organization of the yeast proteome by systematic analysis of protein complexes. *Nature* 415:141-147.

Gheysen D., E. Jacobs, F. de Foresta, C. Thiriart, M. Francotte, D. Thines, and M. De Wilde (1989). Assembly and release of HIV-1 precursor Pr55gag virus-like particles from recombinant baculovirus-infected insect cells. *Cell* 59:103-112.

Gingras A. C., M. Gstaiger, B. Raught, and R. Aebersold (2007). Analysis of protein complexes using mass spectrometry. *Nat. Rev. Mol. Cell. Biol.* 8:645-654.

Gomez C. Y. and T. J. Hope (2006). Mobility of human immunodeficiency virus type 1 Pr55Gag in living cells. *J. Virol.* 80:8796-8806.

Kitajima Y. (2013). Regulation and impairments of dynamic desmosome and carneodesmosome remodeling. *Eur. J. Dermatol.* April 30, E pub ahead of print.

Kraus C., D. Rohde, C. Weidenhammer, G. Qiu, S. T. Pleger, M. Voelkers, M. Boerries, A. Remppis, H. A. Katus, and P. Most (2009). S100A1 in cardiovascular health and disease: closing the gap between basic science and clinical therapy. *J. Mol. Cell. Cardiol.* 47:445-455.

Lewitzky M., C. Kardinal, N. H. Gehring, E. K. Schmidt, B. Konkol, M. Eulitz, W. Birchmeier, U. Schaeper, and S. M. Feller (2001). The C-terminal SH3 domain of the adapter protein Grb2 binds with high affinity to sequences in Gab1 and SLP-76 which lack the SH3-typical P-x-x-P core motif. *Oncogene* 20:1052-1062.

Lukanidin E. and J. P. Sleeman (2012). Building the niche: the role of the S100 proteins in metastatic growth. *Seminars in Cancer Biology* 22:216-225.

Malovannaya A., R. B. Lanz, S. Y. Jung, Y. Bulynko, N. T. Le, D. W. Chan, C. Ding, Y. Shi, N. Yucer, and G. Krenciute, et al. (2011). Analysis of the human endogenous coregulator complexome. *Cell* 145:787-799.

Nigg E. A. (1995). Cyclin-dependent protein kinases: key regulators of the eukaryotic cell cycle. *Bioessays* 17:471-480.

Paul F. E., F. Hosp, and M. Selbach (2011). Analyzing protein-protein interactions by quantitative mass spectrometry. *Methods* 54:387-395.

Prince T., L. Sun, and R. L. Matts (2005). Cdk2: a genuine protein kinase client of Hsp90 and Cdc37. *Biochemistry* 44:15287-15295.

Robinson N. A., S. Lapic, J. F. Welter, and R. L. Eckert (1997). S100A11, S100A10, annexin I, desmosomal proteins, small proline-rich proteins, plasminogen activator inhibitor-2, and involucrin are components of the cornified envelope of cultured human epidermal keratinocytes. *J. Biol. Chem.* 272:12035-12046.

Shioda T. and H. Shibuta (1990). Production of human immunodeficiency virus (HIV)-like particles from cells infected with recombinant vaccinia viruses carrying the gag gene of HIV. *Virology* 175:139-148.

Szymczak A. L., C. J. Workman, Y. Wang, K. M. Vignali, S. Dilioglou, E. F. Vanin, and D. A. Vignali, D. A. (2004). Correction of multi-gene deficiency in vivo using a single "self-cleaving" 2A peptide-based retroviral vector. *Nat. Biotechnol.* 22:589-594.

Venkatesan K., J. F. Rual, A. Vazquez, U. Stelzl, I. Lemmens, T. Hirozane-Kishikawa, T. Hao, M. Zenkner, X. Xin, and K. I. Goh, K. I., et al. (2009). An empirical framework for binary interactome mapping. *Nat. Methods* 6:83-90.

---

What is claimed is:

1. A method of detecting a protein-protein interaction in a cell, the method comprising:
   expressing in the cell a recombinant fusion protein comprising a viral particle-forming polypeptide and a bait polypeptide of interest, wherein the expressed fusion protein forms a protein-protein complex with an endogenously-expressed prey polypeptide within a virus-like particle;
   isolating the virus-like particles from the cell; and
   undertaking a mass spectrometry (MS) analysis of the isolated virus-like particles to detect specific bait-prey protein-protein interactions as compared to background protein-protein interactions from a reference set of virus-like particles comprising viral particle-forming polypeptides not linked to the bait polypeptide of interest;
   thereby detecting the protein-protein interaction in the cell;
   wherein the viral particle-forming polypeptide is an adenovirus particle-forming polypeptide, a HIV particle-forming polypeptide, or a HCV particle-forming polypeptide.

2. The method according to claim 1, wherein the fusion protein comprises a linker between the viral particle-forming polypeptide and the bait polypeptide of interest.

3. The method according to claim 2, wherein the viral particle-forming polypeptide comprises one or more modifications relative to the naturally occurring viral particle-forming protein, wherein the modification is a deletion, mutation, or functional fragment not inhibiting viral particle formation, or is a fusion protein.

4. The method according to claim 1, wherein the endogenously-expressed prey polypeptide is untagged.

5. The method according to claim 1, wherein the recombinant fusion protein and/or the virus-like particle comprises a purification tag.

6. The method according to claim 5, wherein isolating virus-like particles from the cell occurs via the purification tag prior to detecting the presence of the prey polypeptide.

7. The method according to claim 1, wherein the protein-protein interaction was previously unknown or was previously uncharacterized.

8. The method according to claim 1, further comprising forming virus-like particles comprising the protein-protein complex prior to isolating the virus-like particles from the cell.

9. The method according to claim 1, wherein the reference set of virus-like particles comprising viral particle-forming polypeptides not linked to the bait polypeptide of interest comprises a reference set of virus-like particles comprising viral particle-forming polypeptides to a bait polypeptide different from the bait polypeptide of interest.

10. A method of detecting protein-protein interactions in a cell, the method comprising:

expressing in the cell recombinant fusion proteins comprising a viral particle-forming polypeptide and a bait polypeptide of interest, wherein the expressed fusion proteins form a plurality of different protein-protein complexes with a plurality of different endogenously-expressed prey polypeptides within virus-like particles;

isolating the virus-like particles from the cell; and undertaking a mass spectrometry (MS) analysis of the isolated virus-like particles to detect specific bait-prey protein-protein binding interactions as compared to background protein-protein interactions from a reference set of virus-like particles comprising viral particle-forming polypeptides not linked to the bait polypeptide of interest;

thereby detecting the protein-protein interactions in the cell;

wherein the viral particle-forming polypeptide is an adenovirus particle-forming polypeptide, a HIV particle-forming polypeptide, or a HCV particle-forming polypeptide.

11. The method according to claim 1, wherein the reference set of virus-like particles comprising viral particle-forming polypeptides not linked to the bait polypeptide of interest comprises a reference set of virus-like particles comprising viral particle-forming polypeptides to a bait polypeptide different from the bait polypeptide of interest.

* * * * *

SEQUENCE LISTING

```
<160> NUMBER OF SEQ ID NOS: 26

<210> SEQ ID NO 1
<211> LENGTH: 51
<212> TYPE: DNA
<213> ORGANISM: artificial
<220> FEATURE:
<223> OTHER INFORMATION: Primer

<400> SEQUENCE: 1
ctctaaaagc tgcggggccc gctagcgcca ccatgggtgc gagagcgtca g          51
```

<210> SEQ ID NO 2
<211> LENGTH: 54
<212> TYPE: DNA
<213> ORGANISM: artificial
<220> FEATURE:
<223> OTHER INFORMATION: Primer

<400> SEQUENCE: 2
tgtattcggt gaattctgag ctcgtcgacc cgccttgtga cgaggggtcg ctgc        54

<210> SEQ ID NO 3
<211> LENGTH: 30
<212> TYPE: DNA
<213> ORGANISM: artificial
<220> FEATURE:
<223> OTHER INFORMATION: Primer

<400> SEQUENCE: 3
gcgactcgag cggaatcagt ctgattgcgg                                    30

<210> SEQ ID NO 4
<211> LENGTH: 46
<212> TYPE: DNA
<213> ORGANISM: artificial
<220> FEATURE:
<223> OTHER INFORMATION: Primer

<400> SEQUENCE: 4
cgcttctaga ttacatatgg ccgctgcccc gccgctccag aatctc                  46

<210> SEQ ID NO 5
<211> LENGTH: 39
<212> TYPE: DNA
<213> ORGANISM: artificial
<220> FEATURE:
<223> OTHER INFORMATION: Primer

<400> SEQUENCE: 5
gcgacatatg ggcacgcgtg tgcaggtgga aaccatctc                          39

<210> SEQ ID NO 6
<211> LENGTH: 71
<212> TYPE: DNA
<213> ORGANISM: artificial
<220> FEATURE:
<223> OTHER INFORMATION: Primer

<400> SEQUENCE: 6
cgcttctaga ttactcgagt gcggccgcga attctgagct cgtcgacccg ccttccagtt   60
ttagaagctc c                                                        71

<210> SEQ ID NO 7
<211> LENGTH: 83
<212> TYPE: DNA
<213> ORGANISM: artificial
<220> FEATURE:
<223> OTHER INFORMATION: Primer

<400> SEQUENCE: 7
tatggagggc agaggcagcc tgctgacctg cggcgacgtg gaggaaaacc ccggccccga   60
ttacaaggat gacgacgata aga                                           83

<210> SEQ ID NO 8

```
<211> LENGTH: 85
<212> TYPE: DNA
<213> ORGANISM: artificial
<220> FEATURE:
<223> OTHER INFORMATION: Primer

<400> SEQUENCE: 8
cgcgtcttat cgtcgtcatc cttgtaatcg gggccggggt tttcctccac gtcgccgcag      60
gtcagcaggc tgcctctgcc ctcca                                            85

<210> SEQ ID NO 9
<211> LENGTH: 34
<212> TYPE: DNA
<213> ORGANISM: artificial
<220> FEATURE:
<223> OTHER INFORMATION: Primer

<400> SEQUENCE: 9
gaatcggtat tcagcgagtt ccacgatgct gatg                                  34

<210> SEQ ID NO 10
<211> LENGTH: 34
<212> TYPE: DNA
<213> ORGANISM: artificial
<220> FEATURE:
<223> OTHER INFORMATION: Primer

<400> SEQUENCE: 10
catcagcatc gtggaactcg ctgaataccg attc                                  34

<210> SEQ ID NO 11
<211> LENGTH: 29
<212> TYPE: DNA
<213> ORGANISM: artificial
<220> FEATURE:
<223> OTHER INFORMATION: Primer

<400> SEQUENCE: 11
ccccaattga caagtttgta caaaaaagc                                        29

<210> SEQ ID NO 12
<211> LENGTH: 28
<212> TYPE: DNA
<213> ORGANISM: artificial
<220> FEATURE:
<223> OTHER INFORMATION: Primer

<400> SEQUENCE: 12
gggtctagat caaaccactt tgtacaag                                         28

<210> SEQ ID NO 13
<211> LENGTH: 7
<212> TYPE: PRT
<213> ORGANISM: artificial
<220> FEATURE:
<223> OTHER INFORMATION: peptide for Desmoglein 1

<400> SEQUENCE: 13

Thr Gly Lys Leu Thr Leu Lys
1               5

<210> SEQ ID NO 14
<211> LENGTH: 10
<212> TYPE: PRT
<213> ORGANISM: artificial
<220> FEATURE:
```

```
<223> OTHER INFORMATION: peptide for Desmoglein 1

<400> SEQUENCE: 14

Glu Ser Ser Asn Val Val Thr Glu Arg
1               5                   10

<210> SEQ ID NO 15
<211> LENGTH: 7
<212> TYPE: PRT
<213> ORGANISM: artificial
<220> FEATURE:
<223> OTHER INFORMATION: peptide for Desmoglein 1

<400> SEQUENCE: 15

Thr Asn Val Gly Ile Leu Lys
1               5

<210> SEQ ID NO 16
<211> LENGTH: 16
<212> TYPE: PRT
<213> ORGANISM: artificial
<220> FEATURE:
<223> OTHER INFORMATION: peptide for Desmoglein 1

<400> SEQUENCE: 16

Ile Ile Arg Gln Glu Pro Ser Asp Ser Pro Met Phe Ile Ile Asn Arg
1               5                   10                  15

<210> SEQ ID NO 17
<211> LENGTH: 16
<212> TYPE: PRT
<213> ORGANISM: artificial
<220> FEATURE:
<223> OTHER INFORMATION: peptide for Desmoglein 1

<400> SEQUENCE: 17

Ala Leu Asn Ser Met Gly Gln Asp Leu Glu Arg Pro Leu Glu Leu Arg
1               5                   10                  15

<210> SEQ ID NO 18
<211> LENGTH: 32
<212> TYPE: PRT
<213> ORGANISM: artificial
<220> FEATURE:
<223> OTHER INFORMATION: peptide for Desmoglein 1

<400> SEQUENCE: 18

Thr Tyr Val Val Thr Gly Asn Met Gly Ser Asn Asp Lys Val Gly Asp
1               5                   10                  15

Phe Val Ala Thr Asp Leu Asp Thr Gly Arg Pro Ser Thr Thr Val Arg
                20                  25                  30

<210> SEQ ID NO 19
<211> LENGTH: 16
<212> TYPE: PRT
<213> ORGANISM: artificial
<220> FEATURE:
<223> OTHER INFORMATION: peptide for Desmoglein 1

<400> SEQUENCE: 19

Ile Ile Arg Gln Glu Pro Ser Asp Ser Pro Met Phe Ile Ile Asn Arg
1               5                   10                  15

<210> SEQ ID NO 20
<211> LENGTH: 19
<212> TYPE: PRT
```

```
<213> ORGANISM: artificial
<220> FEATURE:
<223> OTHER INFORMATION: peptide for Desmoglein 1

<400> SEQUENCE: 20

Thr Met Asn Asn Phe Leu Asp Arg Glu Gln Tyr Gly Gln Tyr Ala Leu
1               5                   10                  15

Ala Val Arg

<210> SEQ ID NO 21
<211> LENGTH: 16
<212> TYPE: PRT
<213> ORGANISM: artificial
<220> FEATURE:
<223> OTHER INFORMATION: peptide for Desmoglein 1

<400> SEQUENCE: 21

Tyr Val Met Gly Asn Asn Pro Ala Asp Leu Leu Ala Val Asp Ser Arg
1               5                   10                  15

<210> SEQ ID NO 22
<211> LENGTH: 19
<212> TYPE: PRT
<213> ORGANISM: artificial
<220> FEATURE:
<223> OTHER INFORMATION: peptide for Desmoglein 1

<400> SEQUENCE: 22

Thr Met Asn Asn Phe Leu Asp Arg Glu Gln Tyr Gly Gln Tyr Ala Leu
1               5                   10                  15

Ala Val Arg

<210> SEQ ID NO 23
<211> LENGTH: 20
<212> TYPE: PRT
<213> ORGANISM: artificial
<220> FEATURE:
<223> OTHER INFORMATION: peptide for Desmoglein 1

<400> SEQUENCE: 23

Val Val Lys Pro Leu Asp Tyr Glu Ala Met Gln Ser Leu Gln Leu Ser
1               5                   10                  15

Ile Gly Val Arg
            20

<210> SEQ ID NO 24
<211> LENGTH: 19
<212> TYPE: PRT
<213> ORGANISM: artificial
<220> FEATURE:
<223> OTHER INFORMATION: peptide for Desmoglein 1

<400> SEQUENCE: 24

Ile Ser Gly Val Gly Ile Asp Gln Pro Pro Tyr Gly Ile Phe Val Ile
1               5                   10                  15

Asn Gln Lys

<210> SEQ ID NO 25
<211> LENGTH: 22
<212> TYPE: PRT
<213> ORGANISM: artificial
<220> FEATURE:
<223> OTHER INFORMATION: peptide for Desmoglein 1

<400> SEQUENCE: 25
```

Ala Ser Ala Ile Ser Val Thr Val Leu Asn Val Ile Glu Gly Pro Val
1               5                   10                  15

Phe Arg Pro Gly Ser Lys
            20

<210> SEQ ID NO 26
<211> LENGTH: 1049
<212> TYPE: PRT
<213> ORGANISM: Homo sapiens

<400> SEQUENCE: 26

Met Asp Trp Ser Phe Phe Arg Val Val Ala Met Leu Phe Ile Phe Leu
1               5                   10                  15

Val Val Glu Val Asn Ser Glu Phe Arg Ile Gln Val Arg Asp Tyr
        20                  25                  30

Asn Thr Lys Asn Gly Thr Ile Lys Trp His Ser Ile Arg Arg Gln Lys
                35                  40                  45

Arg Glu Trp Ile Lys Phe Ala Ala Ala Cys Arg Glu Gly Glu Asp Asn
    50                  55                  60

Ser Lys Arg Asn Pro Ile Ala Lys Ile His Ser Asp Cys Ala Ala Asn
65                  70                  75                  80

Gln Gln Val Thr Tyr Arg Ile Ser Gly Val Gly Ile Asp Gln Pro Pro
                85                  90                  95

Tyr Gly Ile Phe Val Ile Asn Gln Lys Thr Gly Glu Ile Asn Ile Thr
            100                 105                 110

Ser Ile Val Asp Arg Glu Val Thr Pro Phe Phe Ile Ile Tyr Cys Arg
        115                 120                 125

Ala Leu Asn Ser Met Gly Gln Asp Leu Glu Arg Pro Leu Glu Leu Arg
    130                 135                 140

Val Arg Val Leu Asp Ile Asn Asp Asn Pro Pro Val Phe Ser Met Ala
145                 150                 155                 160

Thr Phe Ala Gly Gln Ile Glu Glu Asn Ser Asn Ala Asn Thr Leu Val
                165                 170                 175

Met Ile Leu Asn Ala Thr Asp Ala Asp Glu Pro Asn Asn Leu Asn Ser
            180                 185                 190

Lys Ile Ala Phe Lys Ile Ile Arg Gln Glu Pro Ser Asp Ser Pro Met
        195                 200                 205

Phe Ile Ile Asn Arg Asn Thr Gly Glu Ile Arg Thr Met Asn Asn Phe
    210                 215                 220

Leu Asp Arg Glu Gln Tyr Gly Gln Tyr Ala Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Gln Ser
            260                 265                 270

Ser Tyr Thr Ile Glu Ile Gln Glu Asn Thr Leu Asn Ser Asn Leu Leu
        275                 280                 285

Glu Ile Arg Val Ile Asp Leu Asp Glu Glu Phe Ser Ala Asn Trp Met
    290                 295                 300

Ala Val Ile Phe Phe Ile Ser Gly Asn Glu Gly Asn Trp Phe Glu Ile
305                 310                 315                 320

Glu Met Asn Glu Arg Thr Asn Val Gly Ile Leu Lys Val Val Lys Pro
                325                 330                 335

Leu Asp Tyr Glu Ala Met Gln Ser Leu Gln Leu Ser Ile Gly Val Arg

```
            340             345             350
Asn Lys Ala Glu Phe His His Ser Ile Met Ser Gln Tyr Lys Leu Lys
        355                 360                 365

Ala Ser Ala Ile Ser Val Thr Val Leu Asn Val Ile Glu Gly Pro Val
    370                 375                 380

Phe Arg Pro Gly Ser Lys Thr Tyr Val Val Thr Gly Asn Met Gly Ser
385                 390                 395                 400

Asn Asp Lys Val Gly Asp Phe Val Ala Thr Asp Leu Asp Thr Gly Arg
                405                 410                 415

Pro Ser Thr Thr Val Arg Tyr Val Met Gly Asn Asn Pro Ala Asp Leu
            420                 425                 430

Leu Ala Val Asp Ser Arg Thr Gly Lys Leu Thr Leu Lys Asn Lys Val
        435                 440                 445

Thr Lys Glu Gln Tyr Asn Met Leu Gly Gly Lys Tyr Gln Gly Thr Ile
    450                 455                 460

Leu Ser Ile Asp Asp Asn Leu Gln Arg Thr Cys Thr Gly Thr Ile Asn
465                 470                 475                 480

Ile Asn Ile Gln Ser Phe Gly Asn Asp Asp Arg Thr Asn Thr Glu Pro
                485                 490                 495

Asn Thr Lys Ile Thr Thr Asn Thr Gly Arg Gln Glu Ser Thr Ser Ser
            500                 505                 510

Thr Asn Tyr Asp Thr Ser Thr Thr Ser Thr Asp Ser Ser Gln Val Tyr
        515                 520                 525

Ser Ser Glu Pro Gly Asn Gly Ala Lys Asp Leu Leu Ser Asp Asn Val
    530                 535                 540

His Phe Gly Pro Ala Gly Ile Gly Leu Leu Ile Met Gly Phe Leu Val
545                 550                 555                 560

Leu Gly Leu Val Pro Phe Leu Met Ile Cys Cys Asp Cys Gly Gly Ala
                565                 570                 575

Pro Arg Ser Ala Ala Gly Phe Glu Pro Val Pro Glu Cys Ser Asp Gly
            580                 585                 590

Ala Ile His Ser Trp Ala Val Glu Gly Pro Gln Pro Glu Pro Arg Asp
        595                 600                 605

Ile Thr Thr Val Ile Pro Gln Ile Pro Pro Asp Asn Ala Asn Ile Ile
    610                 615                 620

Glu Cys Ile Asp Asn Ser Gly Val Tyr Thr Asn Glu Tyr Gly Gly Arg
625                 630                 635                 640

Glu Met Gln Asp Leu Gly Gly Gly Glu Arg Met Thr Gly Phe Glu Leu
                645                 650                 655

Thr Glu Gly Val Lys Thr Ser Gly Met Pro Glu Ile Cys Gln Glu Tyr
            660                 665                 670

Ser Gly Thr Leu Arg Arg Asn Ser Met Arg Glu Cys Arg Glu Gly Gly
        675                 680                 685

Leu Asn Met Asn Phe Met Glu Ser Tyr Phe Cys Gln Lys Ala Tyr Ala
    690                 695                 700

Tyr Ala Asp Glu Asp Glu Gly Arg Pro Ser Asn Asp Cys Leu Leu Ile
705                 710                 715                 720

Tyr Asp Ile Glu Gly Val Gly Ser Pro Ala Gly Ser Val Gly Cys Cys
                725                 730                 735

Ser Phe Ile Gly Glu Asp Leu Asp Asp Ser Phe Leu Asp Thr Leu Gly
            740                 745                 750

Pro Lys Phe Lys Lys Leu Ala Asp Ile Ser Leu Gly Lys Glu Ser Tyr
        755                 760                 765
```

-continued

```
Pro Asp Leu Asp Pro Ser Trp Pro Pro Gln Ser Thr Glu Pro Val Cys
    770             775             780
Leu Pro Gln Glu Thr Glu Pro Val Val Ser Gly His Pro Pro Ile Ser
785             790             795                 800
Pro His Phe Gly Thr Thr Thr Val Ile Ser Glu Ser Thr Tyr Pro Ser
                805             810                 815
Gly Pro Gly Val Leu His Pro Lys Pro Ile Leu Asp Pro Leu Gly Tyr
                820             825             830
Gly Asn Val Thr Val Thr Glu Ser Tyr Thr Thr Ser Asp Thr Leu Lys
            835             840             845
Pro Ser Val His Val His Asp Asn Arg Pro Ala Ser Asn Val Val Val
        850             855             860
Thr Glu Arg Val Val Gly Pro Ile Ser Gly Ala Asp Leu His Gly Met
865             870             875                 880
Leu Glu Met Pro Asp Leu Arg Asp Gly Ser Asn Val Ile Val Thr Glu
                885             890             895
Arg Val Ile Ala Pro Ser Ser Ser Leu Pro Thr Ser Leu Thr Ile His
                900             905             910
His Pro Arg Glu Ser Ser Asn Val Val Val Thr Glu Arg Val Ile Gln
            915             920             925
Pro Thr Ser Gly Met Ile Gly Ser Leu Ser Met His Pro Glu Leu Ala
    930             935             940
Asn Ala His Asn Val Ile Val Thr Glu Arg Val Val Ser Gly Ala Gly
945             950             955                 960
Val Thr Gly Ile Ser Gly Thr Thr Gly Ile Ser Gly Gly Ile Gly Ser
                965             970             975
Ser Gly Leu Val Gly Thr Ser Met Gly Ala Gly Ser Gly Ala Leu Ser
            980             985             990
Gly Ala Gly Ile Ser Gly Gly Gly Ile Gly Leu Ser Ser Leu Gly Gly
            995             1000            1005
Thr Ala Ser Ile Gly His Met Arg Ser Ser Ser Asp His His Phe
    1010            1015            1020
Asn Gln Thr Ile Gly Ser Ala Ser Pro Ser Thr Ala Arg Ser Arg
    1025            1030            1035
Ile Thr Lys Tyr Ser Thr Val Gln Tyr Ser Lys
    1040            1045
```